United States Patent
Bunch et al.

(10) Patent No.: US 9,713,695 B2
(45) Date of Patent: Jul. 25, 2017

(54) DEVICES FOR CREATION OF MULTIPLE VASCULAR ACCESS SITES

(71) Applicant: Intermountain Invention Management, LLC, Salt Lake City, UT (US)

(72) Inventors: T. Jared Bunch, South Jordan, UT (US); Troy Jesse Orr, Draper, UT (US); Brian Stevens, Pleasant Grove, UT (US)

(73) Assignee: Intermountain Invention Management, LLC, Salt Lake City, UT (US)

( * ) Notice: Subject to any disclaimer, the term of this patent is extended or adjusted under 35 U.S.C. 154(b) by 285 days.

(21) Appl. No.: 14/292,099

(22) Filed: May 30, 2014

(65) Prior Publication Data
US 2014/0358087 A1    Dec. 4, 2014

Related U.S. Application Data

(60) Provisional application No. 61/829,180, filed on May 30, 2013.

(51) Int. Cl.
| A61M 5/00 | (2006.01) |
| A61M 25/00 | (2006.01) |
| A61M 25/01 | (2006.01) |
| A61M 25/06 | (2006.01) |
| A61B 17/34 | (2006.01) |

(52) U.S. Cl.
CPC ........ *A61M 25/0097* (2013.01); *A61M 25/01* (2013.01); *A61B 2017/3411* (2013.01); *A61M 25/0606* (2013.01); *A61M 2210/12* (2013.01)

(58) Field of Classification Search
CPC .......... A61M 2210/12; A61M 25/0097; A61M 25/0606; A61M 25/01; A61M 39/02; A61M 39/105; A61B 2017/3411; A61B 90/11
See application file for complete search history.

(56) References Cited

U.S. PATENT DOCUMENTS

| 4,978,334 A | 12/1990 | Toye et al. |
| 5,190,528 A | 3/1993 | Fonger et al. |
| 5,380,290 A | 1/1995 | Makower et al. |
| 5,797,835 A | 8/1998 | Green |
| 5,941,499 A | 8/1999 | Wollschlager |
| 6,120,494 A | 9/2000 | Jonkman |
| 6,183,443 B1 | 2/2001 | Kratoska et al. |
| 6,589,262 B1 | 7/2003 | Honebrink et al. |
| 6,626,869 B1 | 9/2003 | Bint |

(Continued)

FOREIGN PATENT DOCUMENTS

EP    2366422    9/2011

OTHER PUBLICATIONS

International Search Report and Written Opinion dated Sep. 26, 2014 for PCT/US2014/040269.

*Primary Examiner* — Rebecca E Eisenberg
(74) *Attorney, Agent, or Firm* — Stoel Rives LLP

(57) ABSTRACT

Various medical procedures benefit from the creation of multiple access sites in a single anatomical vessel. For example, in some cardiac procedures, a plurality of catheters may be introduced into a single blood vessel through a corresponding plurality of access sites. The present application discloses devices for creating multiple access sites in a vessel and methods of using the same.

25 Claims, 21 Drawing Sheets

(56) References Cited

U.S. PATENT DOCUMENTS

| | | | |
|---|---|---|---|
| 6,695,818 | B2 | 2/2004 | Wollschlager |
| 6,746,466 | B2 | 6/2004 | Eidenschink et al. |
| 6,986,749 | B2 | 1/2006 | Wollschlager |
| 7,722,567 | B2 | 5/2010 | Tal |
| 7,794,489 | B2 | 9/2010 | Shumer et al. |
| 8,377,006 | B2 | 2/2013 | Tal et al. |
| 2003/0208206 | A1 | 11/2003 | Gitis et al. |
| 2004/0220588 | A1 | 11/2004 | Kermode et al. |
| 2006/0135973 | A1 | 6/2006 | Hawkins et al. |
| 2008/0027457 | A1 | 1/2008 | Dienst et al. |
| 2009/0112182 | A1* | 4/2009 | Razavi ................ A61M 25/00 604/507 |
| 2009/0163766 | A1 | 6/2009 | Torrie et al. |
| 2010/0241106 | A1* | 9/2010 | Torrie ................ A61B 17/175 606/1 |
| 2011/0276002 | A1 | 11/2011 | Bierman |
| 2012/0157854 | A1 | 6/2012 | Kurrus et al. |

* cited by examiner

DEVICES FOR CREATION OF MULTIPLE VASCULAR ACCESS SITES

CROSS-REFERENCE TO RELATED APPLICATIONS

This application claims the benefit of U.S. Provisional Patent Application No. 61/829,180, filed on May 30, 2013, titled DEVICES FOR CREATION OF MULTIPLE VASCULAR ACCESS SITES, the disclosure of which is incorporated herein by reference in its entirety.

BACKGROUND

Various medical procedures benefit from the creation of multiple access sites in a single vessel. For example, in some cardiac procedures, a plurality of catheters may be introduced into a single blood vessel through a corresponding plurality of access sites. Embodiments discussed below can be used in such multi-site contexts, and represent advancements over known techniques for the creation of such sites. However, the present disclosure is not necessarily limited to such procedures.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

Various medical procedures benefit from the creation of multiple access sites in a single vessel. For example, in some cardiac procedures, a plurality of catheters may be introduced into a single blood vessel through a corresponding plurality of access sites. Traditional methods for creating multiple sites can suffer from drawbacks. For example, such methods may take a relatively long time to perform, may have numerous steps, and/or may include complicated or redundant steps. In some instances, each access site into the vessel is created individually, or independently from the other access sites. Thus, each introducer needle used to create the separate access sites may be imaged (e.g., via ultrasound) during placement within the vessel. Embodiments disclosed herein can be used in such contexts and may ameliorate or resolve one or more of the foregoing drawbacks and/or other drawbacks not mentioned above. Such improvements will be evident from the discussion that follows. It is also noted that the advantages and uses of various embodiments are not necessarily limited to the procedures just mentioned.

Figure 1:
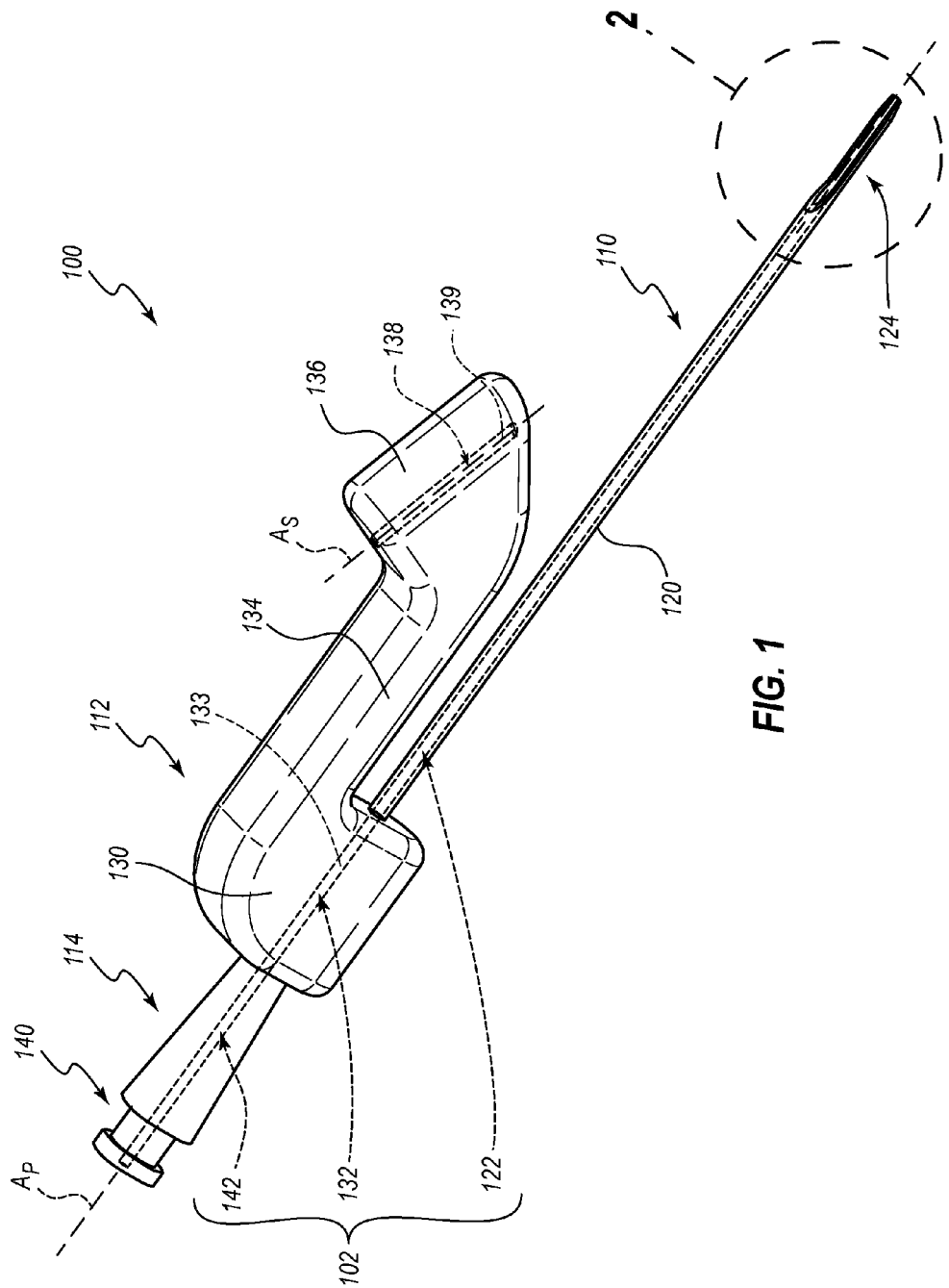
FIG. 1 is a perspective view of an embodiment of a device for creating multiple access sites in a vessel.

FIG. 1 is a perspective view of an embodiment of a device 100 that can be used to create multiple access sites in an anatomical vessel. The device may be used with any suitable anatomical vessel, such as a blood vessel or other tubular structure. In the illustrated embodiment, the device includes a shaft 110, a hub 112, and a connector 114. The shaft 110 of the illustrated embodiment is permanently coupled to the hub 112, although such a permanent mounting may not be present in other embodiments, as discussed further below. The connector 114 may likewise be permanently mounted to the hub 112.

In the illustrated embodiment, the shaft 110 comprises a substantially rigid tube 120, which may resemble a dilator, needle, or other rigid elongated device, such as may be commonly introduced into a patient during catheterization or other such procedures. The tube 120 may define a lumen 122. A distal tip 124 may have a specialized configuration, as discussed further below with respect to FIG. 2.

A proximal end of the tube 120 is permanently coupled to a primary region 130 of the hub 112. The hub 112 further includes a transition region 134 and a secondary region 136. In the illustrated embodiment, the hub 112 substantially resembles an S-shaped handle, and in some embodiments, the hub 112 may be used as a handle. Accordingly, in some embodiments, the transition region 134 and/or one or more of the primary and secondary regions 130, 136 may be ergonomically shaped for comfortable and/or efficient gripping by a medical practitioner.

In the illustrated embodiment, the primary region 130 is generally shaped as a generally rectangular block that defines a fluid channel or lumen 132, which can be in fluid communication with the lumen 122 of the tube 120. Specifically, an inner surface 133 of the primary region 130 can define the lumen 132. The transition region 134 can extend distally from the primary region 130. The secondary region 136 may extend transversely outwardly from, and in some embodiments may further extend distally from, the transition region 134. In the illustrated embodiment, the secondary region 136 is shaped substantially as a wedge-shaped block that defines a fluid channel or lumen 138. Specifically, an inner surface 139 of the secondary region 136 can define the lumen 138.

In the illustrated embodiment, the primary lumen 132 and the secondary lumen 138 are angled relative to each other. Stated otherwise, the primary lumen 132 can define a longitudinal axis $A_P$ and the secondary lumen 138 can define a longitudinal axis $A_S$ that are angled relative to each other. As is more apparent in the cross-sectional view FIG. 2, in the illustrated embodiment, the longitudinal axes $A_P$, $A_S$ can be contained within the same plane (e.g., the plane of the page in FIG. 2). Such an arrangement may aid in the guiding of a shaft into the lumen 138 such that the shaft contacts the distal end 124 of the tube 120 at an interior of a vessel, as discussed further below.

The connector 114 may extend proximally from the primary region 130 of the hub 112. The connector 114 may define a lumen 142 that is in fluid communication with the lumens 132, 122 discussed above. In the illustrated embodiment, the lumens 142, 132, 122 are collinear. Together, the lumens 142, 132, 122 can define a unitary lumen 102 of the device 100.

The connector 114 may include a luer interface 140, which in the illustrated embodiment is a female luer interface. Such an interface may facilitate connection with a syringe for any suitable purpose, such as fluid delivery via the lumen 102 into the vessel or aspiration of blood from the vessel via the lumen 102. Any other suitable medical device may be connected with the connector 114 via any suitable connection or interface.

Figure 2:
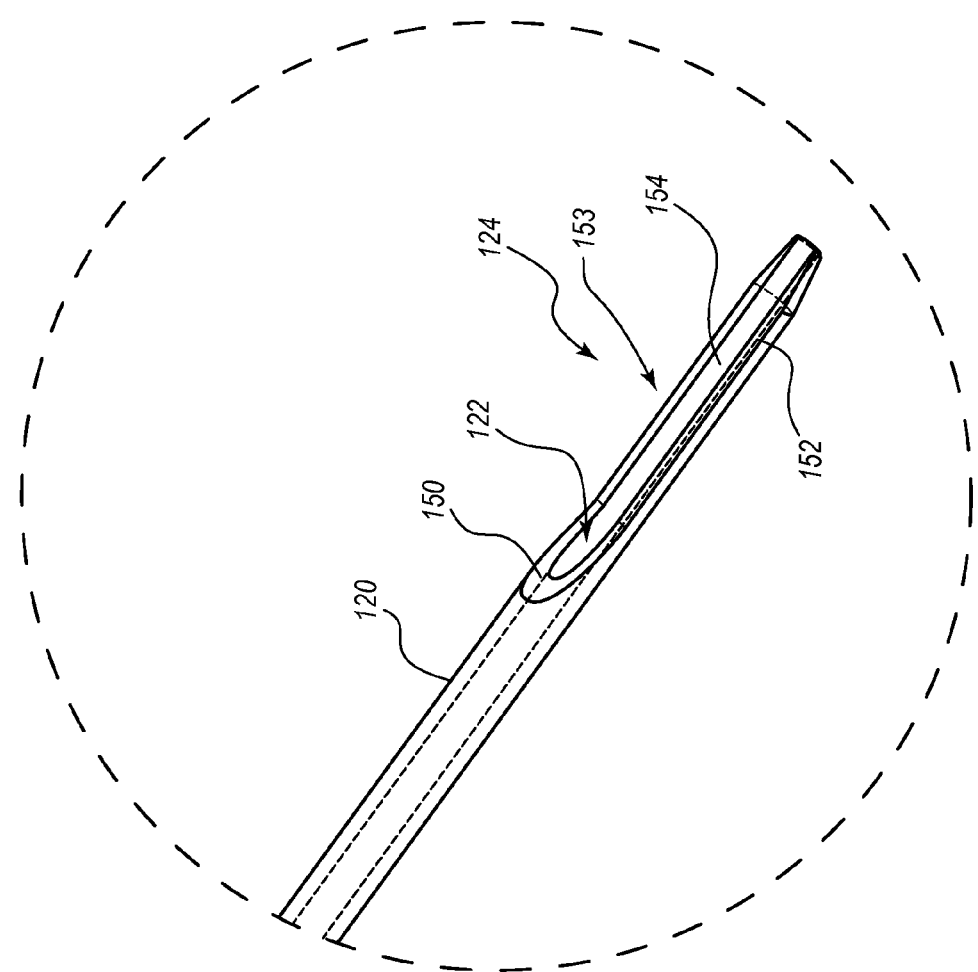
FIG. 2 is an enlarged perspective view of a distal end of an embodiment of a shaft portion of the device of FIG. 1 taken along the view line 2 shown in FIG. 1.
Figure 3A:
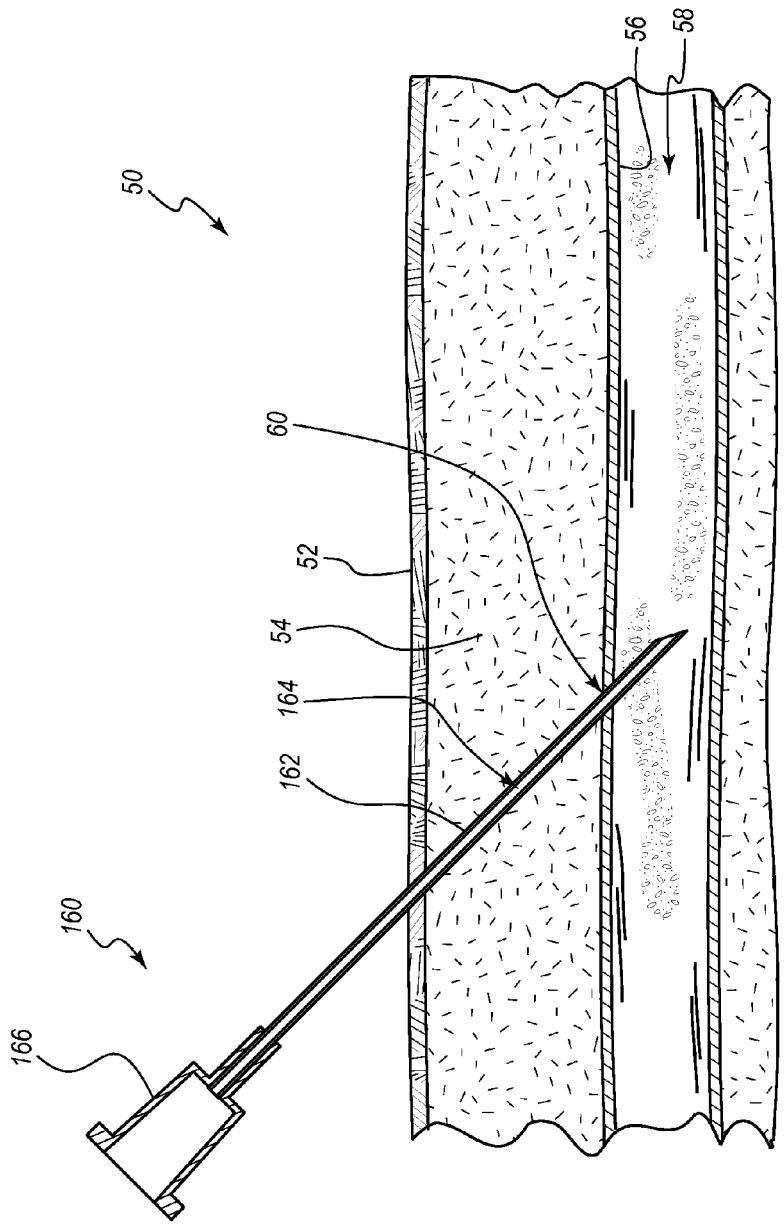
FIG. 3A is a cross-sectional view of an introducer needle being inserted into an interior of a vessel in an early stage of an illustrative procedure for creating multiple access sites into the vessel.
Figure 3B:
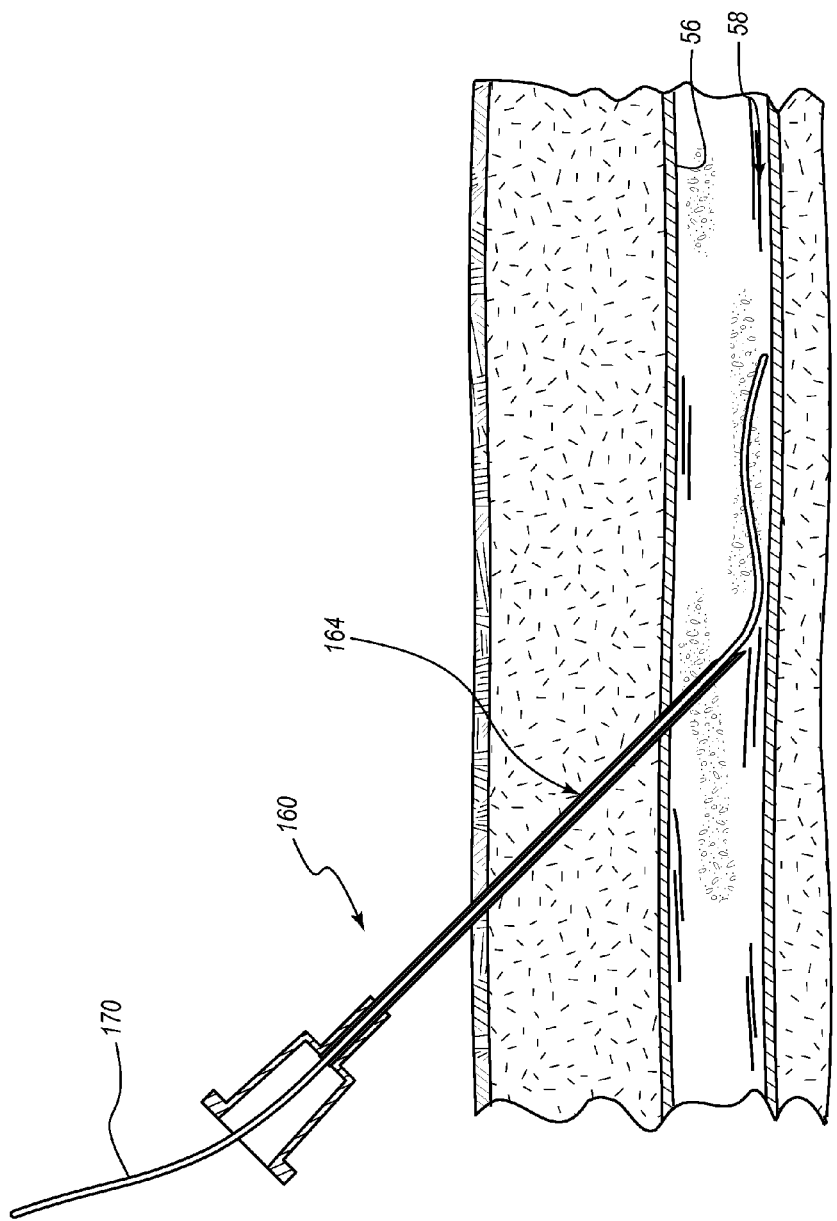
FIG. 3B is a cross-sectional view of a further stage of the procedure at which a guide wire has been advanced through the introducer needle into a lumen of the vessel.
Figure 3C:
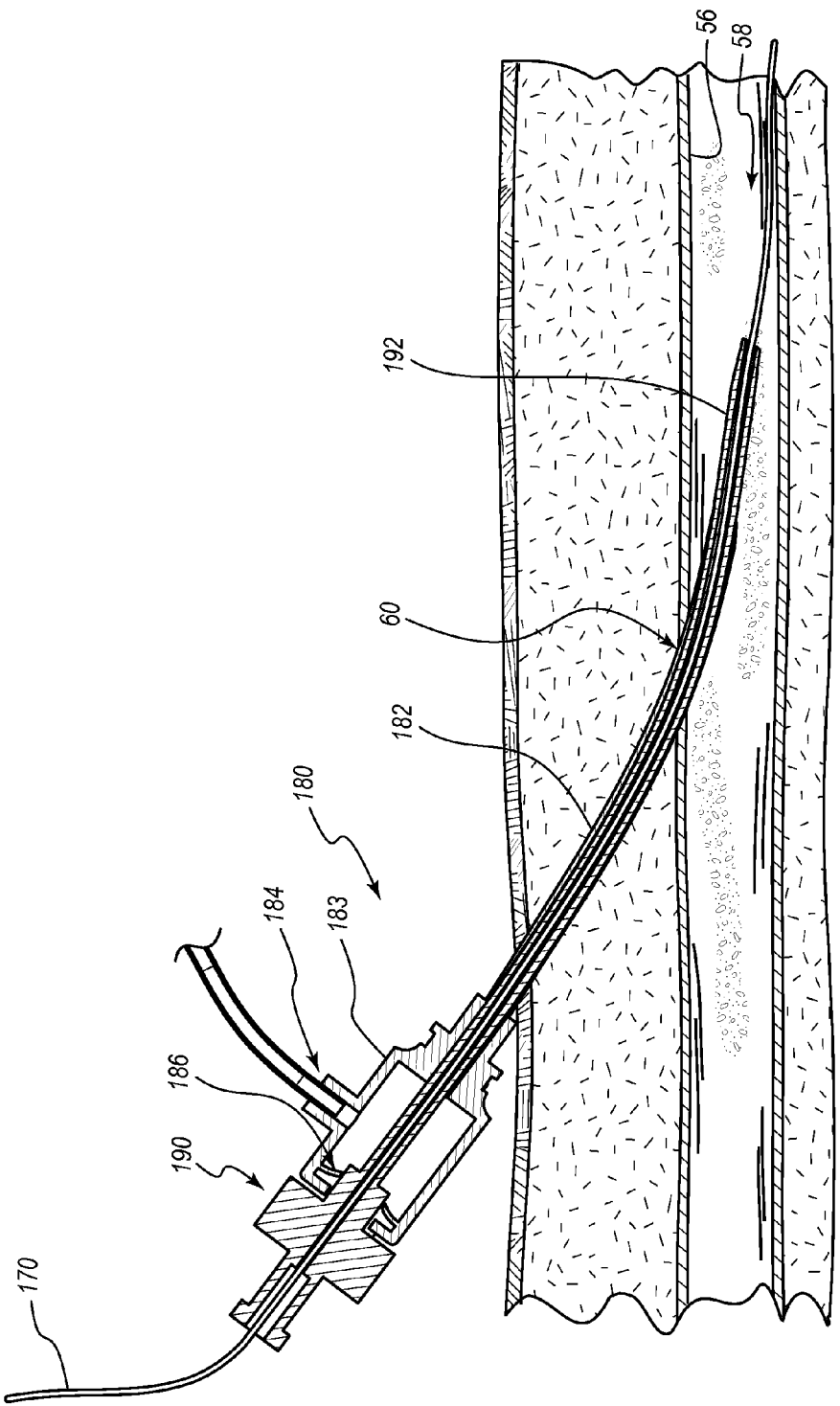
FIG. 3C is a cross-sectional view of a further stage of the procedure at which the introducer needle has been removed from the patient and an embodiment of an introducer and an embodiment of a dilator have been inserted into the vessel over the guide wire.
Figure 3D:
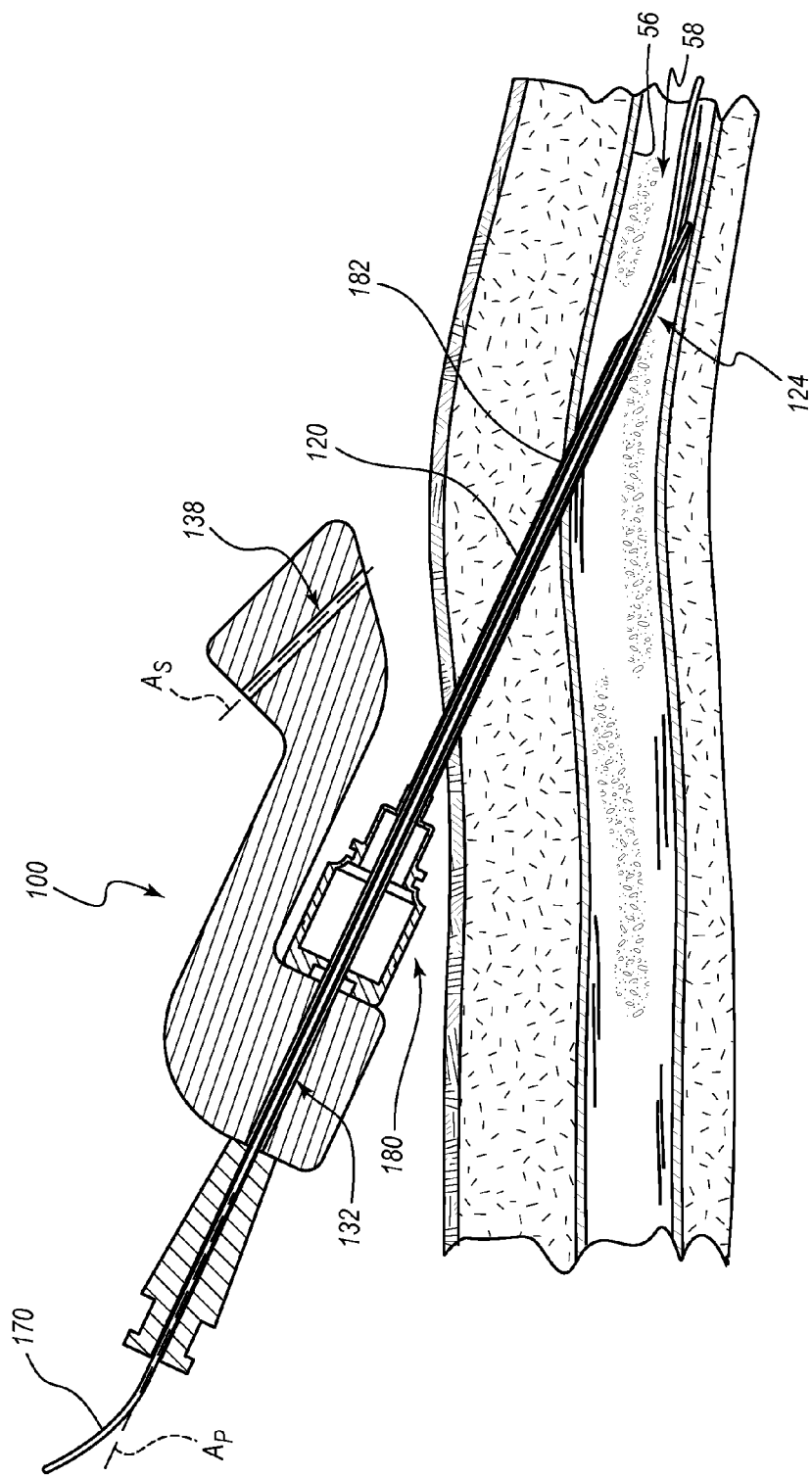
FIG. 3D is a cross-sectional view of a further stage of the procedure at which the dilator has been removed from the introducer and the shaft portion of the device of FIG. 1 has been inserted into the vessel through the introducer.
Figure 3E:
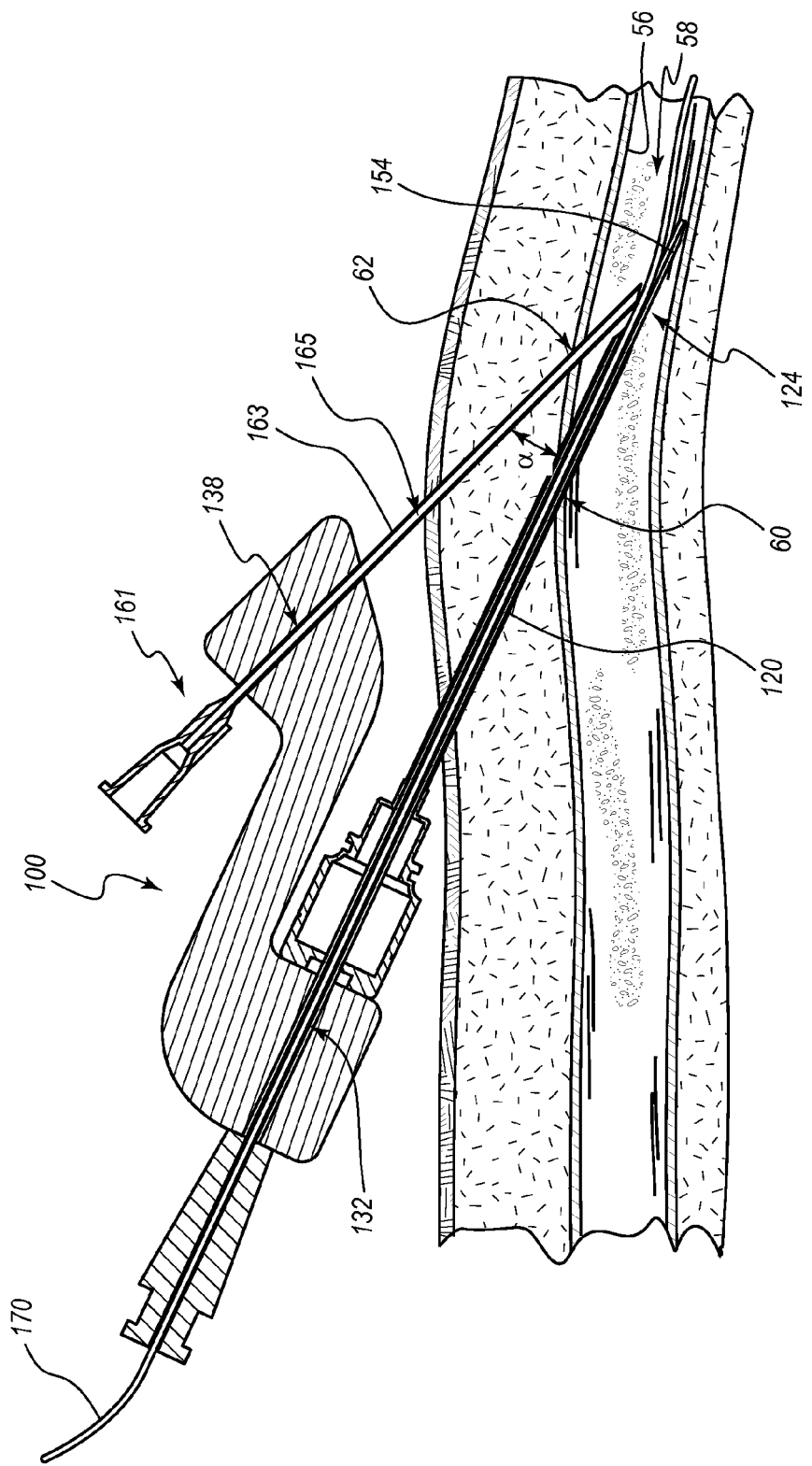
FIG. 3E is a cross-sectional view of a further stage of the procedure at which an introducer needle has been inserted through a channel defined by the device of FIG. 1 and into the vessel.

With reference to FIG. 2, the distal end 124 of the tube 120 may have a shape that is particularly suited for receiving and/or stopping a distal end of a secondary shaft that is inserted into the secondary lumen of the hub 112 at an interior of a vessel (see FIG. 3E). In the illustrated embodiment, the tube 120 is shaped substantially as a hollow cylinder in regions proximal to the distal end 124. However, the distal end 124 is notched so as to expose an interior surface of the tube 120. In particular, a beveled face 150 and a longitudinally extending face 152 represent a notched region. The distal end 124 further includes a platform 154 that is configured to receive and/or stop the distal end of the secondary shaft. In the illustrated embodiment, the platform 154 is substantially semi-cylindrical. The notched region and platform 154 of the illustrated embodiment may generally be referred to as a stopping region, a backstop region, or a secondary shaft interface 153 of the tube 120.

FIGS. 3A-3E depict various stages of an illustrative procedure for creating multiple access sites into the vessel. As further discussed with reference to these drawings, in some embodiments, after a first shaft has been positioned within a blood vessel through a first vascular access site, that shaft may be used in positioning a distal end of another shaft (e.g., that of an introducer needle) into the blood vessel via a second vascular access site. Creation of the first vascular access site may proceed in any suitable manner, such as via traditional methods using an introducer needle and/or methods that employ portions of a specialized device 100, such as that depicted in FIGS. 1-2. Accordingly, in some embodiments, imaging of any suitable variety (e.g., ultrasound) is used to situate the first introducer needle within the vessel. However, in some embodiments, formation of one or more additional vascular access sites can be accomplished without further use of such imaging techniques. Such an approach can facilitate and/or accelerate procedures for the creation of multiple access sites in a single vessel. Other and/or further advantages are also possible, such as, for example, a reduced likelihood of back-puncturing the vessel when creating the second or subsequent access sites due to the stopping capabilities provided by the devices, systems, and techniques disclosed herein.

FIG. 3A is a cross-sectional view of an early stage of an illustrative procedure for creating multiple access sites in a vessel 56. The vessel 56 can define a lumen 58, and is positioned subcutaneously within a patient 50. In particular, the vessel 56 can be positioned beneath the skin 52 and subcutaneous tissue 54 of the patient 50. An introducer needle 160 can be inserted through a wall of the vessel at an insertion site or access site 60 and into an interior of the vessel 56 (e.g., to a position within the lumen 58) in any suitable manner. For example, in some instances, any suitable imaging technique (e.g., ultrasound or fluoroscopy) may be used to ensure that a distal end of the introducer needle 160 enters the lumen 58 without passing all the way through the vessel 56 (e.g., without puncturing both a front wall and a back wall of the vessel, but rather, puncturing the front wall only). In the illustrated embodiment, the introducer needle 160 includes a needle shaft 162 that defines a lumen 164. The introducer needle 160 further includes a connector 166, such as a female luer, for connecting with any other suitable medical device (e.g., a syringe) for any suitable purpose (e.g., aspiration, flushing, etc.).

FIG. 3B is a cross-sectional view of a further stage of the procedure at which a guide wire 170 has been advanced through the lumen 164 of the introducer needle 160 into the lumen 58 of the vessel 56. Any suitable technique for such advancement of the guide wire 170 into the vessel 56 is contemplated.

FIG. 3C is a cross-sectional view of a further stage of the procedure at which the introducer needle 160 has been removed from the patient and an embodiment of a sheath introducer 180 and an embodiment of a dilator 190 have been inserted into the vessel 56 over the guide wire 170. Any suitable technique for insertion of the introducer 180 and the dilator 190 is contemplated. The illustrated introducer 180 and dilator 190 are of a standard variety. The introducer 180 includes a sheath 182 that has been inserted into the vessel 56 via the access site 60. The introducer 180 further includes a hub 183 that defines a port 184 for any suitable purpose (aspiration, line flushing, etc.). The hub 183 may include a hemostatic valve 186. The illustrated dilator 190 includes a relatively flexible shaft 192 configured to pass over the guide wire 170. The shaft 192 is shown extending within the lumen 58 of the vessel 56 beyond a distal end of the sheath 182 of the introducer 180.

FIG. 3D is a cross-sectional view of a further stage of the procedure at which the dilator 190 has been removed from the introducer 180 and the shaft portion, or tube 120, of the device 100 has been inserted into the vessel 56 through the introducer 180 and over the guide wire 170. The distal end 124 of the tube 120 extends distally beyond the distal end of the sheath 182 of the introducer 180. As previously mentioned, the axes $A_P$, $A_S$ defined by the channels 132, 138, respectively, can extend at an angle relative to each other, and in the illustrated embodiment, the axes $A_P$, $A_S$ are contained within the same plane.

FIG. 3E is a cross-sectional view of a further stage of the procedure at which an additional introducer needle 161 has been inserted into the channel 138, through the skin of the patient, and into the vessel 56 to form a second access site 62 into the vessel. The introducer needle 161 can include a shaft 163 that defines a lumen 165.

The introducer needle 161 can be inserted into the vessel 56 without imaging of the patient relative to the introducer needle 161, or without imaging the introducer needle 161. For example, the device 100 can permit the introducer needle 161 to be inserted along a predetermined path, or along a path that is constrained relative to the tube 120. As a result, a distal tip of the introducer needle 161 can enter the vessel 56 and then come into contact with the platform 154 of the distal tip 124. The platform 154 can stop the distal tip and provide tactile feedback to the practitioner that the tip of the introducer needle 161 is within the vessel 56. The platform 154 can prevent the tip of the introducer needle 161 from passing through a back wall of the vessel 56. Stated otherwise, the distal end 124 of the tube 120 can aid in positioning the distal tip of the introducer needle 161 within the vessel 56 and/or can aid in maintaining the tip within the vessel 56. In some embodiments, the distal tip of needle 161 may not be in physical contact with the platform 154, but instead be disposed adjacent to or proximate to the platform.

In the illustrated embodiment, the shaft or tube 120 and the shaft 163 are each linear elements that are aligned with the longitudinal axes $A_P$, $A_S$. In the configuration shown in FIG. 3E, the tube 120 and the shaft 163 extend at an angle α relative to each other. As previously discussed, the illustrated axes $A_P$, $A_S$ are coplanar along the plane defined by the page. A longitudinal axis defined by the vessel 56 may also be contained within the same plane. In other embodiments, the axes $A_P$, $A_S$ may be angled relative to each other by a different amount and may be contained within a different plane. In still other embodiments, one or more of the tube 120 and the shaft 163 may be, or may have portions that are, non-linear. Examples of certain of such embodiments are discussed below with respect to FIGS. 6 and 7.

In an embodiment, the shaft or tube 120 and the shaft 163 are at an angle relative to one another such that the first and second longitudinal axes $A_P$, $A_S$ intersect.

Figure 3F:
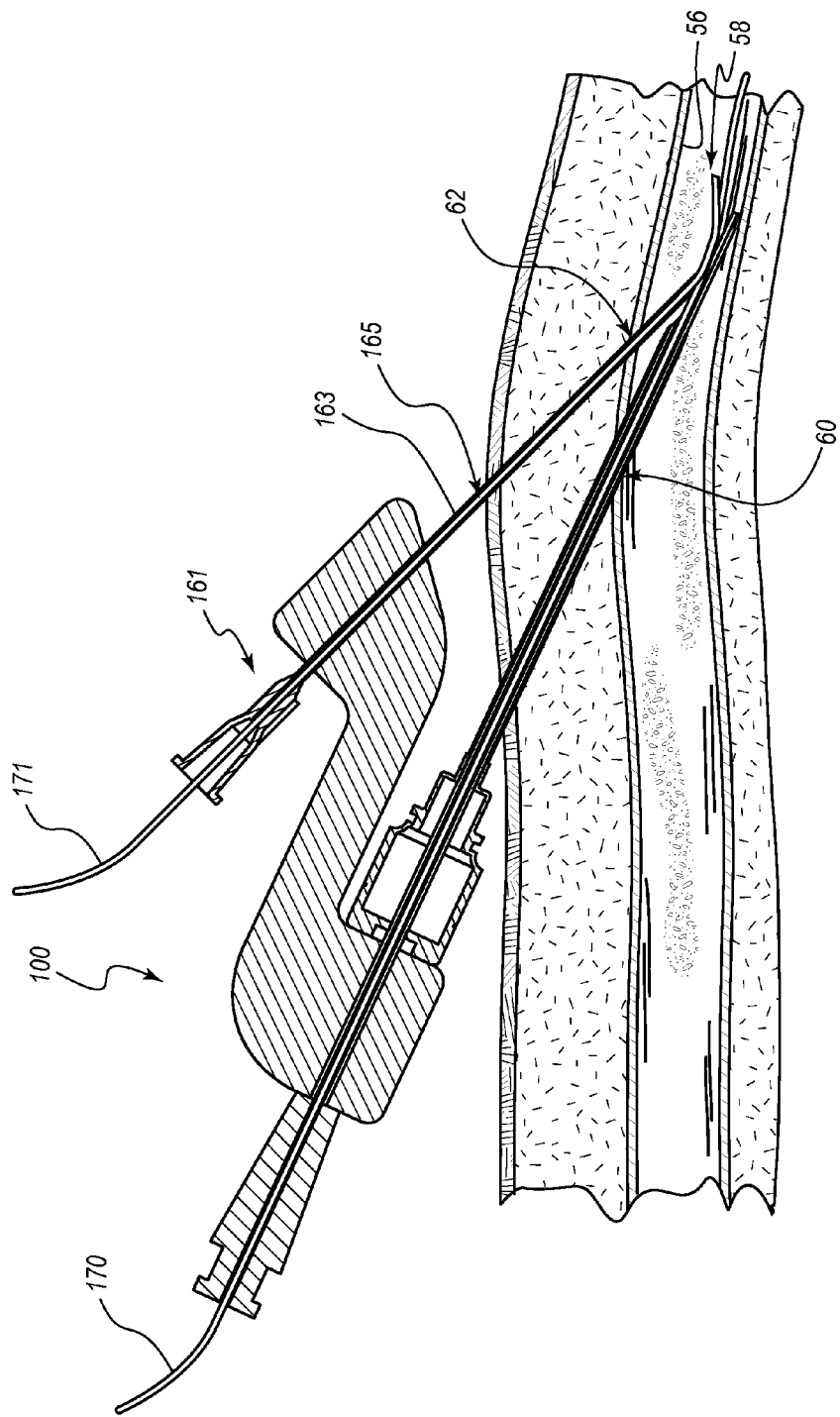
FIG. 3F is a cross-sectional view of a further stage of the procedure at which a second guide wire has been inserted into the vessel through the newly placed introducer needle.

FIG. 3F is a cross-sectional view of a further stage of the procedure at which a second guide wire 171 has been inserted into the vessel 56 through the introducer needle 161. With the two guide wires 170, 171 in place, the two access sites 60, 62 into the vessel 56 are well established, and may be used in any suitable manner.

In subsequent stages, the device 100, the introducer 190, and/or the introducer needle 161 may be removed individually or concurrently over the guide wires 170, 171. One or more further vascular access devices may be inserted in one or more of the access sites 60, 62 over one or more of the guide wires 170, 171, as needed or desired.

In some embodiments, after removal of the device 100, the introducer 190, and/or the introducer needle 161, a third access site into the vessel 56 may be formed in a manner similar to that depicted in FIGS. 3C-3F, but using the guide wire 171. That is, the steps or stages illustrated in FIGS. 3C-3F may be repeated using the guide wire 171. For example, an introducer and dilator may be inserted over the guide wire 171, and the dilator may be subsequently removed in a manner such as that shown in and discussed with respect to FIGS. 3C-3D. A device such as the device 100 described above may then be inserted into the introducer in a manner such as that shown in and discussed with respect to FIG. 3D. An introducer needle may then be inserted into the device and into the vessel 56 in a manner such as that shown in and discussed with respect to FIG. 3E. A third guide wire may then be introduced into the vessel via the introduce needle in a manner such as that shown in and discussed with respect to FIG. 3F. In some instances, such methods may be repeated multiple times to form additional access sites.

Figure 4:
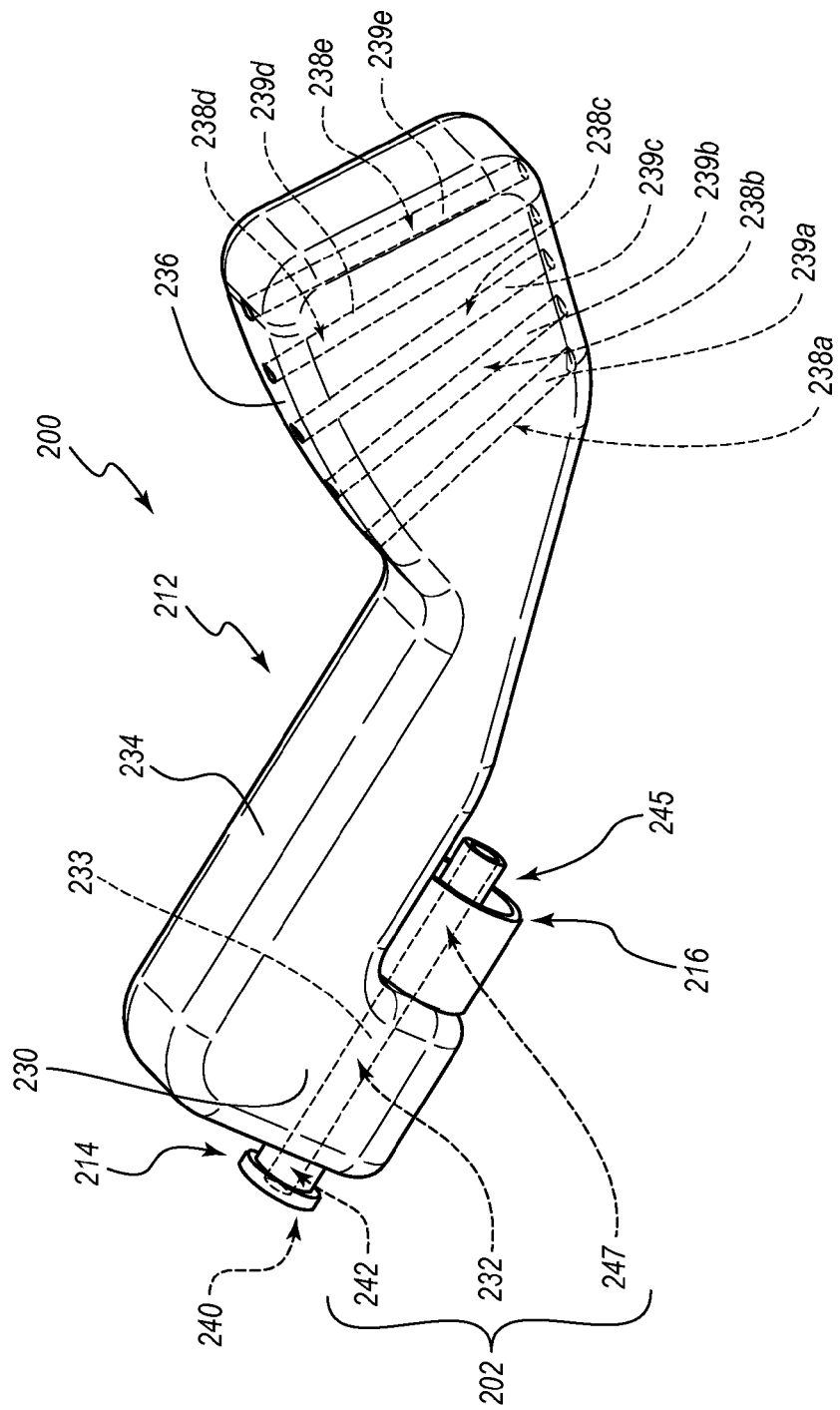
FIG. 4 is a perspective view of another embodiment of a device for creating multiple access sites in a vessel.

FIG. 4 is a perspective view of another embodiment of a device 200 for creating multiple access sites in a vessel. The device 200 can resemble the device 100 in many respects. Accordingly, like features are designated with like reference numerals, with the leading digits incremented to "2." Relevant disclosure set forth above regarding similarly identified features thus may not be repeated hereafter. Moreover, specific features of the device 200 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the device 200. Any suitable combination of the features and variations of the same described with respect to the device 100 can be employed with the device 200, and vice versa. This pattern of disclosure applies equally to further embodiments depicted in subsequent figures and described hereafter, wherein the leading digits may be further incremented.

Figure 5:
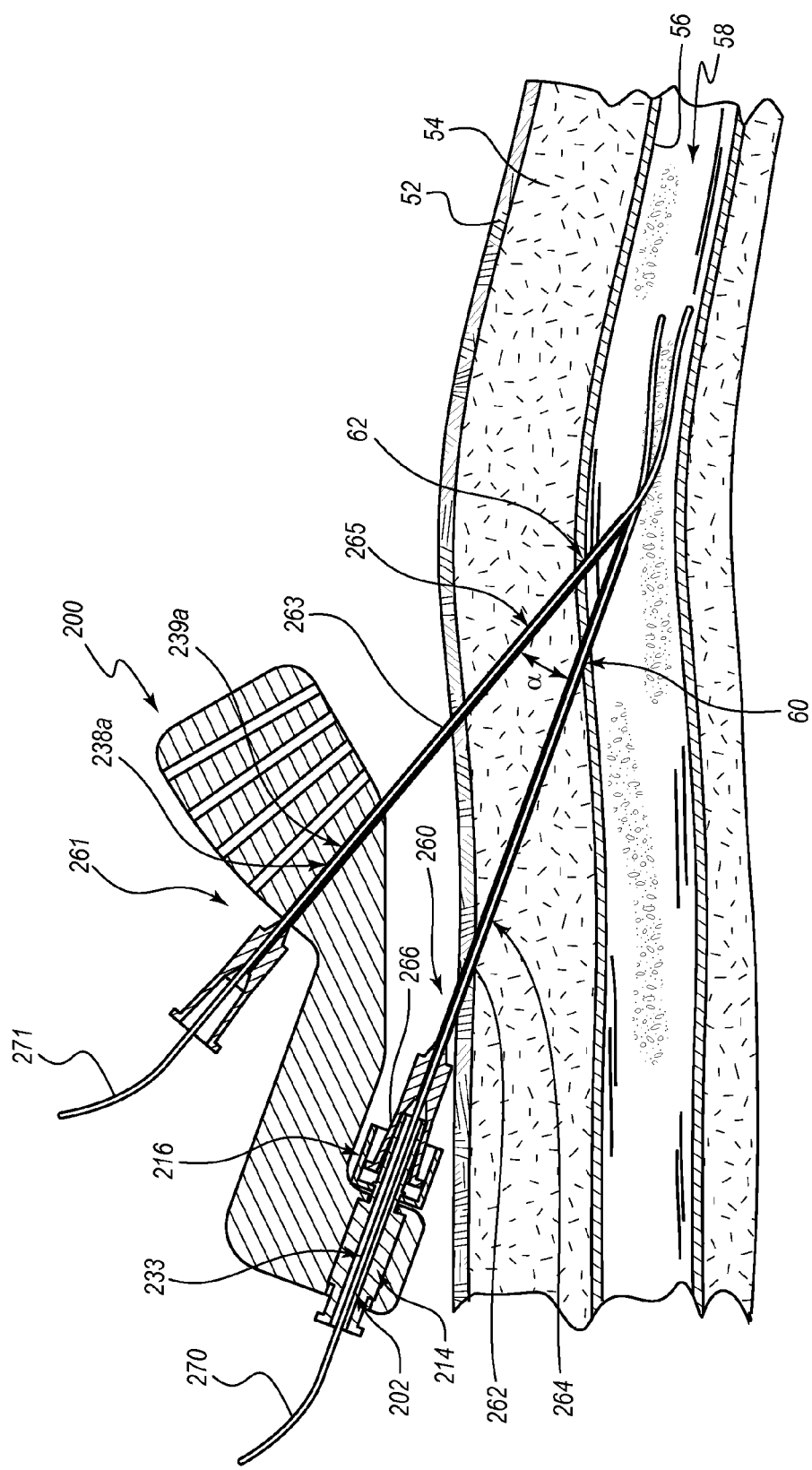
FIG. 5 is a cross-sectional view of the device of FIG. 4 in use in a stage of another illustrative procedure for creating multiple access sites into a vessel.

The device 200 includes a hub 212, a proximal connector 214, and a distal connector 216. The hub 212 may include a primary region 230, a transition region 234, and a secondary region 236. The proximal connector 214 may resemble the connector 114 described above, and may include a female luer, in some embodiments. The distal connector 216 may be positioned at a distal end of a primary region 230 of the hub 212. As shown in FIG. 5, the distal connector 216 may be configured to be removably coupled with a connector 266 of an introducer needle 260. In some embodiments, the distal connector 216 comprises a male luer 245.

The device primary region 230 can define a lumen 232—specifically, an inner wall 233 of the primary region 230 may define the lumen 232. The proximal and distal connectors 214, 216 may similarly define lumens 242, 247 that are in fluid communication with the lumen 232, and the device 200 thus may have a unitary lumen or channel 202 that extends through a portion thereof.

The secondary region can include a plurality of lumens or channels 238a, 238b, 238c, 238d, 238f, 238e, each of which may be used to form an access site into a vessel. In some embodiments, a practitioner may select any of the channels 238a, 238b, 238c, 238d, 238f, 238e for a desired placement of the second access site. In other or further instances, a practitioner may use multiple channels 238a, 238b, 238c, 238d, 238f, 238e in conjunction with the channel 202 to form three or more access sites into the vessel. In the illustrated embodiment, each channel 238a, 238b, 238c, 238d, 238f, 238e is defined by an inner sidewall 239a, 239b, 239c, 239d, 239e that extends through an entirety of the secondary region 236.

With reference to FIG. 5, illustrative methods for using the device 200 may differ from those discussed above with respect to the methods relative to the device 100. For example, in some embodiments, the introducer needle 260 is inserted into the vessel 56. Either before or after this insertion event, the distal connector 216 of the device 200 may be attached to the connector 266 of the insertion needle 260. A guide wire 270 may also be inserted into the vessel 56 at the first insertion site 60.

With the first introducer needle 260 in place, a second introducer needle 261 can be introduced into the vessel 56. Any of the channels 238a, 238b, 238c, 238d, 238f, 238e may be used. In the illustrated procedure, the channel 238a is used. The second introducer needle 261 can be advanced into the channel 238a, through the skin of the patient, and then into the vessel 56 until a distal end of the second introducer needle 261 contacts and/or is stopped by the distal end of the first introducer needle 260. A second guide wire 271 may be inserted into the vessel via the second access site 62 thus formed.

In some embodiments, the device 200 may be used to create three or more access sites in the vessel 56 without removing the first and/or the second needles 260, 261. For example, in some embodiments, with one or more of the first and second needles 260, 261 in place, a third introducer needle may be inserted into one of the remaining four channels 238b, 238c, 238d, 238e of the device 200 and through another portion of the vessel wall.

Figure 6:
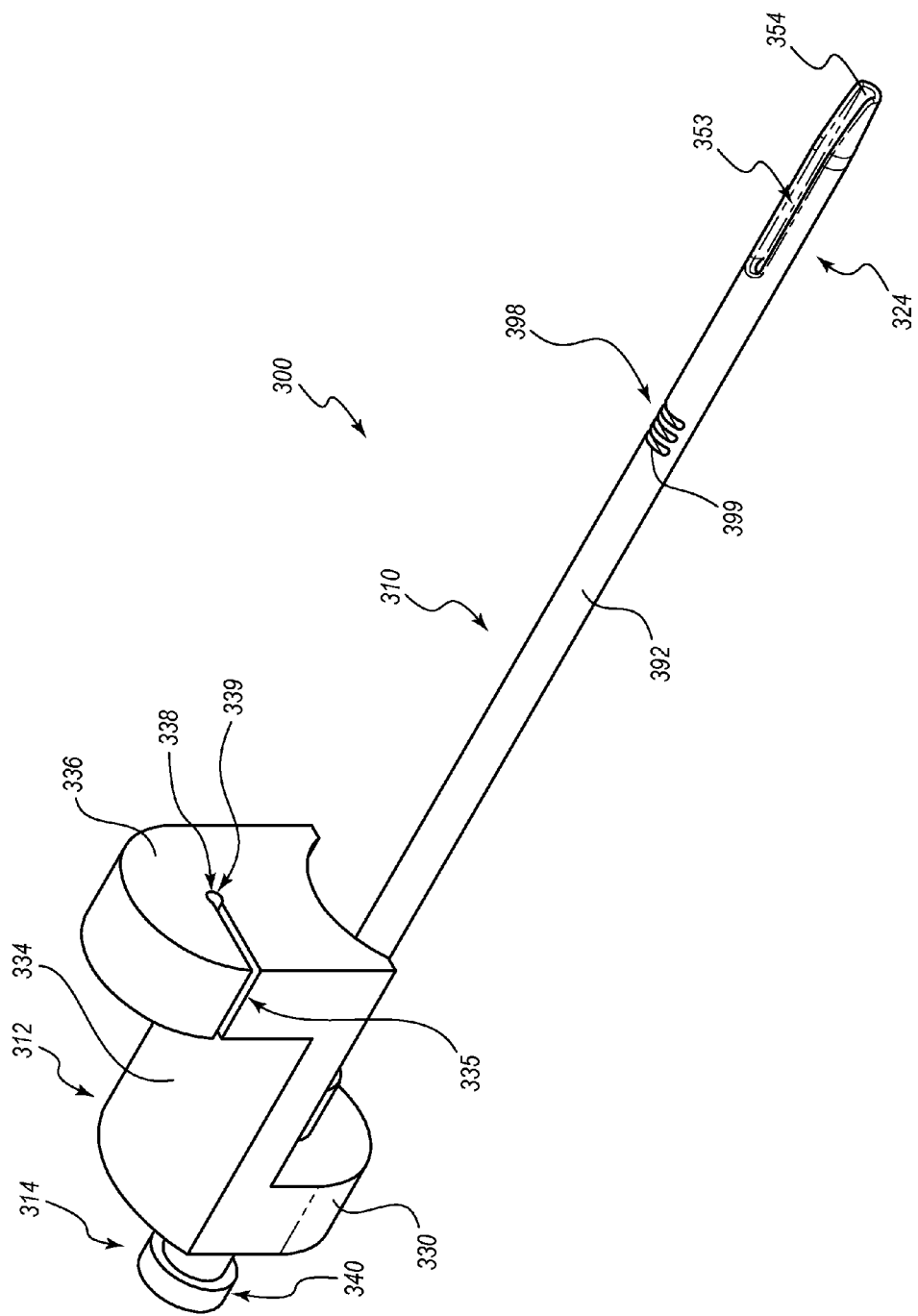
FIG. 6 is a perspective view of yet another embodiment of a device for creating multiple access sites in a vessel.

FIG. 6 is a perspective view of yet another embodiment of a device 300 for creating multiple access sites in a vessel. The device 300 includes a shaft 310 that is permanently attached to a hub 312. In further embodiments, the device 300 includes a connector 314 attached to the hub 312. The hub 312 includes a primary region 330, a transition region 334, and a secondary region 336. The secondary region 336 can include a channel 338, which may be defined by a sidewall 339. In some embodiments, the secondary region 336 further includes a slit 335. The channel 338 and/or the slit 335 may extend substantially parallel to the shaft 310.

The shaft 310 can include a shaft 392 similar to the dilator shaft 192 described above. However, the shaft 392 can include a bending region 398 that is configured to permit a distal end 324 of the shaft 310 to bend relative to a proximal portion thereof. In the illustrated embodiment, the bending region 398 includes grooves 399 at one side of the shaft 310. The grooves 399 can permit the shaft 310 to bend in a predetermined direction. Bending of the shaft 310 can be about an axis that is perpendicular to the longitudinal axis $A_P$ of the shaft 310, as shown in FIG. 7.

Figure 7:
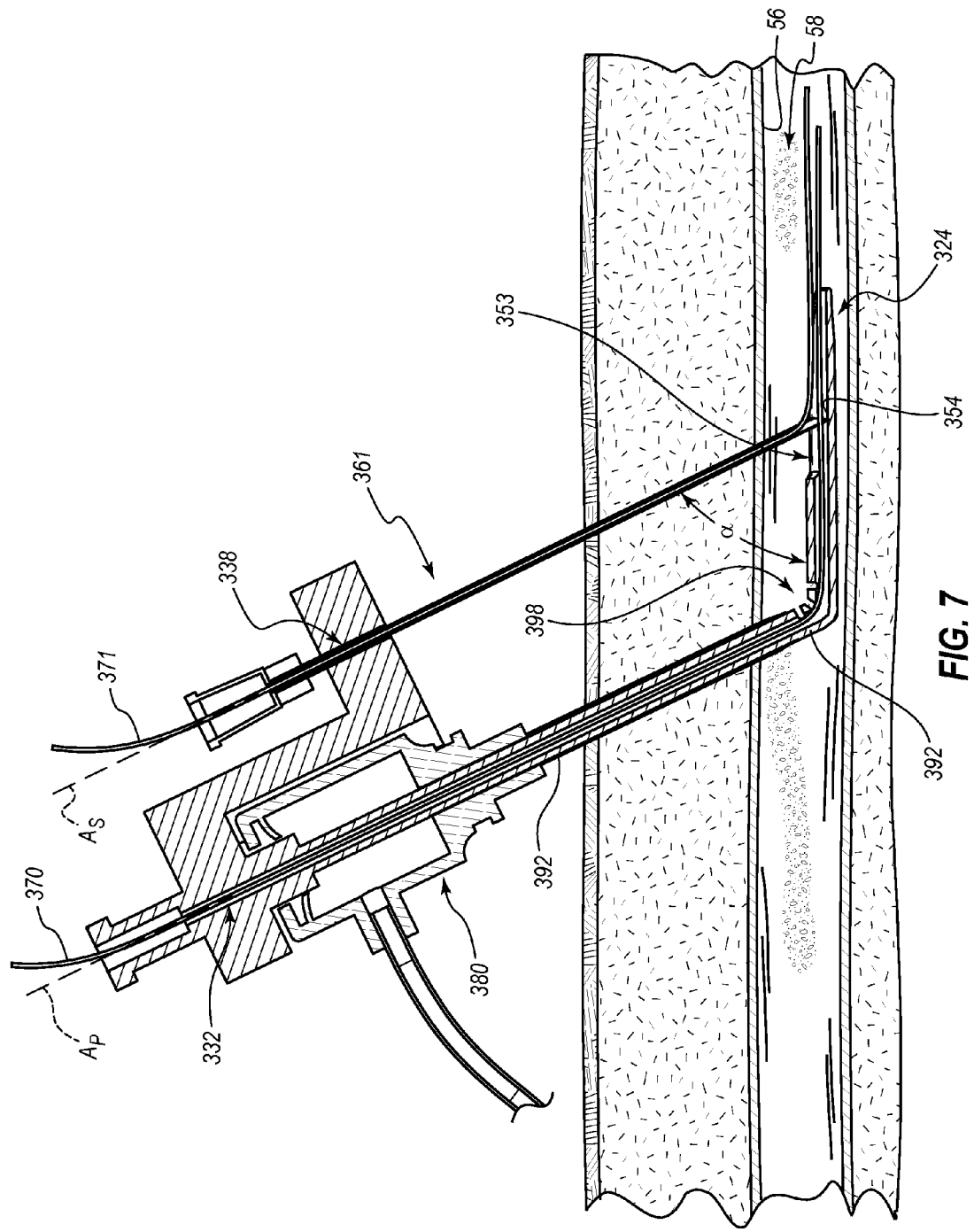
FIG. 7 is a cross-sectional view of the device of FIG. 6 in use in a stage of yet another illustrative procedure for creating multiple access sites into a vessel.

FIG. 7 is a cross-sectional view of the device of FIG. 6 in use in a stage of yet another illustrative procedure for creating multiple access sites into a vessel. The shaft 310 of the device 300 has been inserted through an introducer 380. The distal end 324 of the shaft 310 has been bent within the vessel 56 so as to be at an angle relative to the proximal portion of the shaft 310 and so as to generally align with (or be parallel to) a longitudinal axis of the vessel 56. A notched region 353 of the distal end 324 may face upward, or toward the surface of the skin to provide an opening to the platform 354. The distal end of an introducer needle 361 that has been passed into the channel 338 may come into contact with and be stopped by the platform 354 within the vessel 56. In some embodiments, the distal end of needle 361 may not contact the platform 354, but instead be disposed adjacent to or proximate to the platform.

Figure 8:
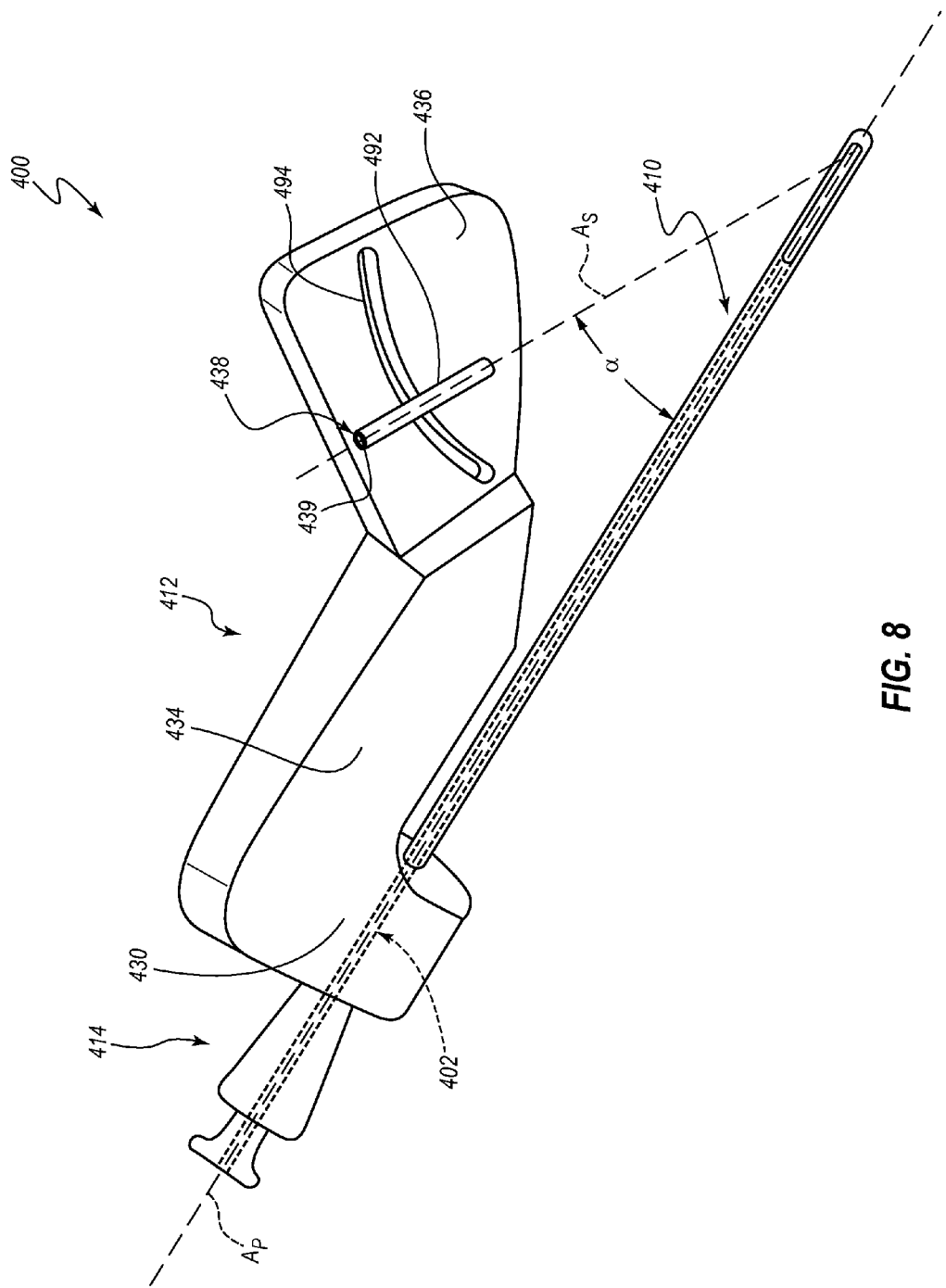
FIG. 8 is a perspective view of a still further embodiment of a device for creating multiple access sites in a vessel.

FIG. 8 depicts another embodiment of a device 400 for creating multiple access sites in a vessel. The device 400 includes a shaft 410 that is permanently attached to a hub 412. A connector 414 is attached to the hub 412 as well. The device includes a primary lumen 402.

The hub 412 includes a primary region 430 and a transition region 434 such as the like-named regions 230, 234 described above. However, the hub 412 includes a secondary region 436 that varies somewhat from the secondary region 236 described above. In particular, the secondary region 436 includes a track 494, which may also be referred to as a groove or path, and further includes a constraining device, such as a tube 492, that is movable along the track 494. The movable element, shown as tube 492, defines a secondary lumen or channel 438 and is movably coupled to the hub 412. Specifically, the channel 438 may be defined by an inner wall 439 of the tube 492. Stated otherwise, the secondary channel 438 is defined by the separate tube 492 that is attached to the hub 412, rather than by the hub 412 itself.

The tube 492 is movable relative to the hub 412. For example, a practitioner may be able to select an angle $\alpha$ that a secondary introducer needle may define relative to the primary shaft 410. Certain of such embodiments may resemble the devices 100, 200. Rather than fixed channels 138, 238, however, the attached tube 492 or other needle restricting element defines the channel 438 through which an introducer needle is advanced toward the vessel.

Figure 9:
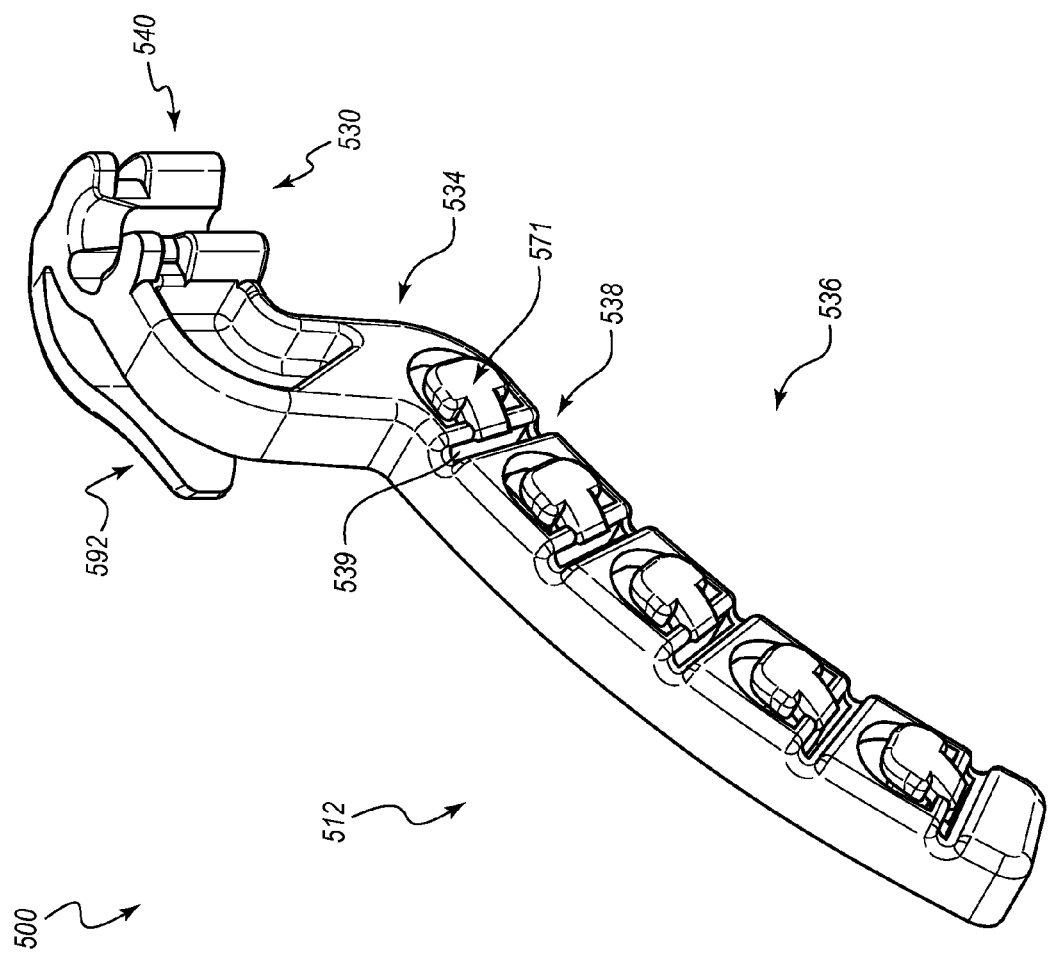
FIG. 9 is a perspective view of an additional embodiment of a device for creating multiple access sites in a vessel.

FIG. 9 depicts an additional embodiment of a device 500 for creating multiple access sites in a vessel. In the illustrated embodiment, the device 500 includes a hub 512, which includes a primary region 530, a transition region 534, and a secondary region 536 such as the like-named regions 230, 234, 236 described above. The hub 512 may include an interface 540, which in the illustrated embodiment is generally a female luer-type interface configured to accept a male luer-type connector coupled to, or of, the primary introducer needle. Any suitable medical device may be connected with the hub 512 via any suitable connector which may be coupled to interface 540. Unlike previous embodiments, however, the connector of the primary introducer needle is releasably connected to hub 512.

The primary region 530 of the hub 512 may also include a flange 592, which may extend from the primary region 530 toward the secondary region 536. The flange 592 is configured to couple to and transiently expand an opening comprising the interface 540, which is configured to accept and secure a primary introducer needle or a connector coupled to the primary introducer needle. The material used for flange 592 in such an embodiment may be relatively rigid but still flexible enough to allow for the temporary expansion of an opening comprising the interface 540 with pressure applied by, for example, a practitioner's hand, and allow for the opening to grip a primary introducer needle when the pressure is released. Upon release, or prior to expansion, the interface 540 provides sufficient force upon the introducer needle such that the needle does not move appreciably when the device 500 is used for any suitable purpose (e.g., aspiration, flushing, vascular access, etc.).

Figure 10A:
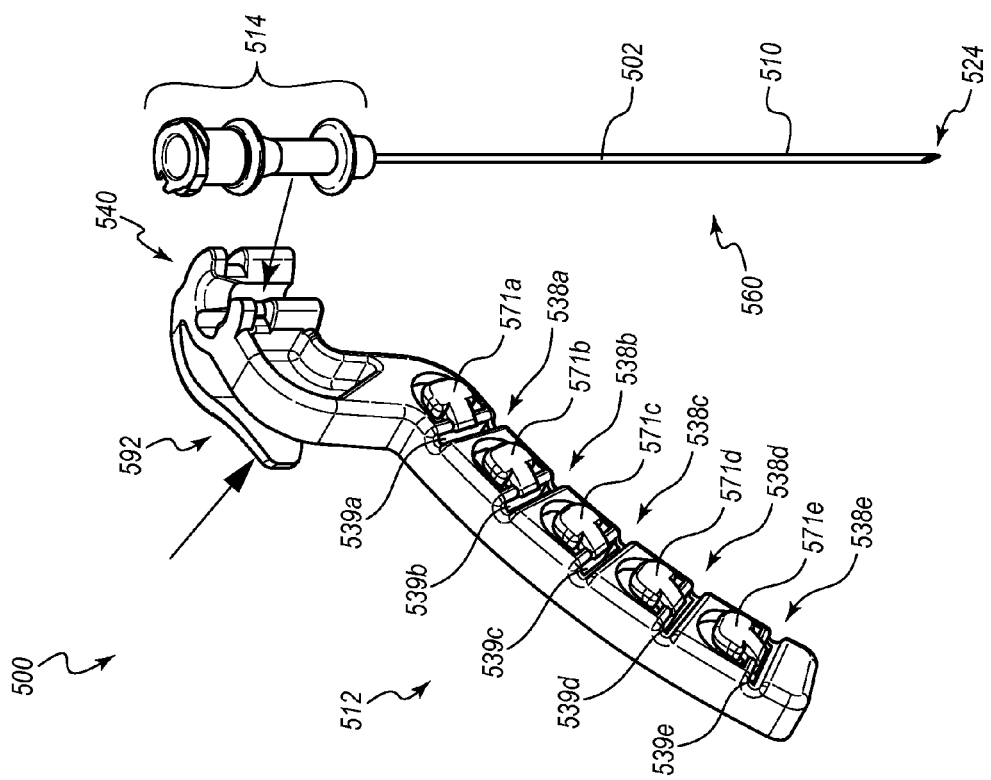
FIG. 10A is a perspective view of a primary introducer needle being inserted into an illustrative embodiment of a device for creating multiple access sites in a vessel.
Figure 10B:
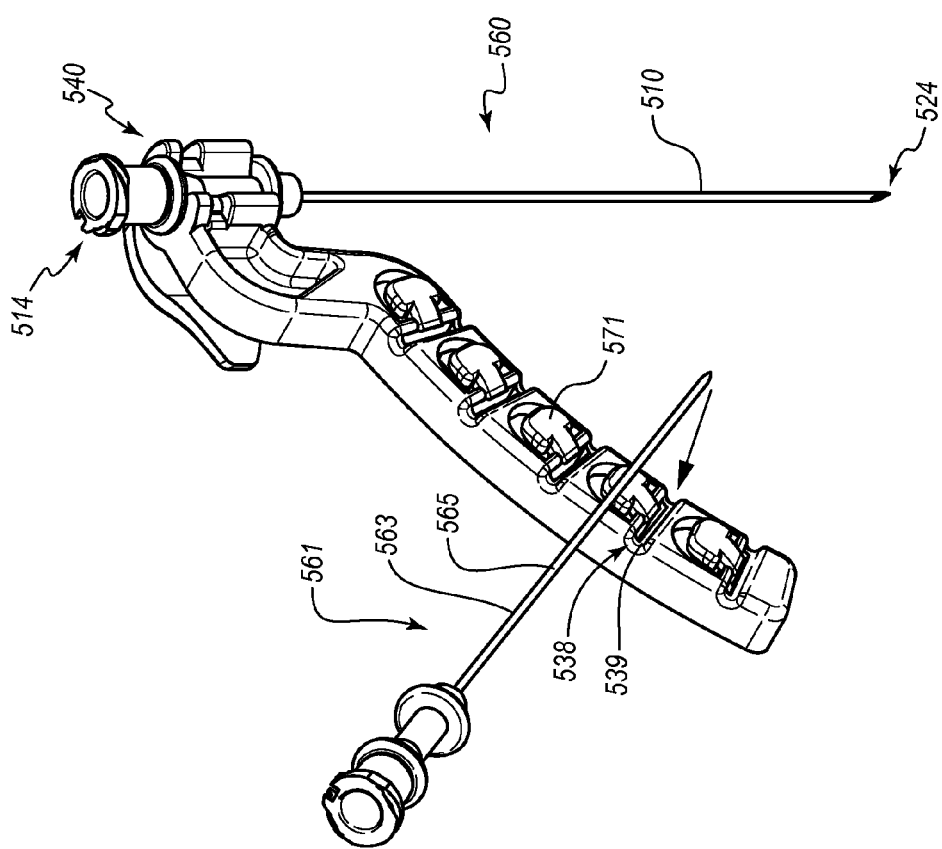
FIG. 10B is a perspective view of a secondary introducer needle being inserted into an illustrative embodiment of a device for creating multiple access sites in a vessel, which already contains a primary introducer needle.
Figure 10C:
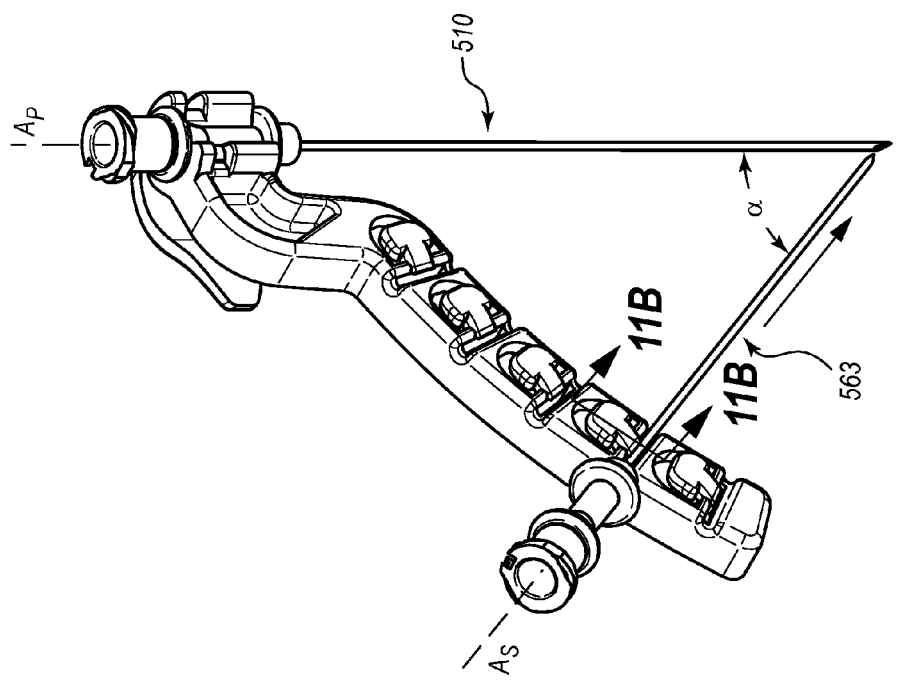
FIG. 10C is a perspective view of a primary and a secondary introducer needle present in illustrative embodiment of a device for creating multiple access sites in a vessel.

The secondary region 536 of the device 500 can include a channel 538, which may be defined by a sidewall 539. The channel 538 may extend substantially perpendicular to the longitudinal axis of secondary region 536, and is accessible laterally, or from the side of the hub as illustrated in FIGS. 10A-10C, to accept a secondary introducer needle. The lateral opening of channel 538 may be configured to permit a shaft of the secondary introducer needle to be placed into, or disposed in, the second channel. The openings of multiple channels 538 provides lateral access for a plurality of secondary introducer needles to be disposed in hub 512.

The secondary region 536 may further include a deflectable element which may widen the opening of channel 538 to allows access to the channel and/or to grip and maintain the secondary introducer needle releasably within the hub 512. The deflectable element is in communication with, or coupled to, the channel 538 comprising an inner sidewall 539.

In an embodiment, the deflectable element may be a protuberance or button 571, which may be aligned with a longitudinal axis of a secondary introducer needle. The button 571 is configured to transiently expand the opening of the channel to accept or release the secondary needle. Depression of the button 571 moves the deflectable element such that the shaft of the secondary introducer needle can be disposed into the channel 538 via the lateral opening.

FIGS. 10A, 10B and 10C depict the device 500 of FIG. 9 for creating multiple access sites in a vessel, showing the insertion of a primary introducer needle 560 and a secondary introducer needle 561. In the illustrated embodiment, the device 500 has an interface 540 configured to couple to the primary needle 510 via connector 514, with channels 538a, 538b, 538c, 538d, 538e each comprising at least an inner sidewall 539a, 539b, 539c, 539d, 539e and each of which may be accessed by a button 571a, 571b, 571c, 571d, 571e.

As shown in FIG. 10A, the device 500 includes a primary introducer needle 560 with a fluid channel or lumen 502, shaft 510, distal tip 524 and connector 514 that is releasably coupled to hub 512 via interface 540. An introducer needle 560 comprising a primary shaft 510, may include a connector 514. The connector 514 can releasably couple to hub 512 via interface 540, which may be configured to connect any suitable primary introducer needle with a primary shaft 510 to hub 512. The connector 514 may comprise a male luer or luer-type connector which is not releasably coupled to the primary needle 560.

FIG. 10B depicts the device 500 with the primary introducer needle 560 releasably coupled thereto via connector 514 and interface 540, and shows the disposition of secondary introducer needle 561. The secondary introducer needle 561 can include a shaft 563 that defines a lumen 565. A deflectable element, here button 571, is depressed to transiently expand the opening of channel 538, and the shaft 563 of the secondary introducer needle 561 is inserted into the channel 538.

The material used for secondary hub region 536 in such an embodiment may be relatively rigid but still flexible enough to allow for expansion of a channel with pressure applied by, for example, a practitioner's finger. Upon release of the deflectable element (i.e. button 571), or prior to its deflection, the channel 538 comprising at least one sidewall 539, retains the shaft 563 of the secondary introducer needle 561. The inner sidewall 539 provides sufficient force upon the secondary needle 561 such that the needle does not move appreciably when the device 500 is used for any suitable purpose (e.g., aspiration, flushing, vascular access, etc.).

FIG. 10C is a perspective view of a primary and a secondary introducer needle present in illustrative embodiment of a device for creating multiple access sites in a vessel. In the illustrated embodiment, the shaft 510 of primary introducer needle 560 and the shaft 563 of the secondary introducer needle 561 are angled relative to each other at an angle $\alpha$. Stated otherwise, the primary lumen of primary introducer needle 560 can define a longitudinal axis $A_P$ and the secondary lumen (565) of secondary introducer needle 561 can define a longitudinal axis $A_S$ that are angled relative to each other. In certain embodiments, the longitudinal axes $A_P$, $A_S$ can be contained substantially within the same plane. In some embodiments, the longitudinal axes $A_P$, $A_S$ can be configured to intersect, and may occur either with or without the shafts 510 and 563 coming in physical contact with each other (e.g., the shafts may be disposed adjacent to or proximate to each other without contact).

In a similar manner as described for an embodiment of a device for creating multiple access sites in a vessel shown in FIG. 9, multiple secondary introducer needles 561 can be introduced into the vessel after placement of the primary introducer needle 560, by appropriate placement in the secondary hub region 536. Any of the channels 538a, 538b, 538c, 538d, 538e may be used to accept the secondary needle shaft, with each channel defined by an inner sidewall 539a, 539b, 539c, 539d, 539e.

The one or multiple secondary needles 561 can be advanced into one of the multiple channels 538, through the skin of the patient, and then into a vessel. In an embodiment, a distal end of the secondary needle 561 contacts, is configured to stop and/or is stopped by the distal end of the first introducer needle 560. Alternatively, the length of the secondary needle 561 is such that when the connector region of the secondary needle 561 abuts the secondary hub region 536, the distal end of the secondary needle is disposed adjacent to or proximate to the distal end of the first introducer needle 560. In an embodiment, the distal end of the secondary needle is configured to stop adjacent to or proximate to the distal end of the first introducer needle 560.

The introducer needle 561 can be inserted into a vessel and may eliminate the need for imaging of the patient relative to the introducer needle 561, or without imaging the introducer needle 561. The device 500 can permit the secondary introducer needle 561 (or a plurality of needles 561) to be inserted along a predetermined and/or a constrained path relative to the path of the primary introducer needle 560.

The device 500 may be suitably configured to constrain the angle α between, and relative to, each of the axes $A_P$, $A_S$ of the primary and secondary introducer needles. The device 500 may be suitably configured to also, or alternatively, constrain the depth of the distal tip of the primary and/or secondary introducer needles within the vessel.

Figure 11C:
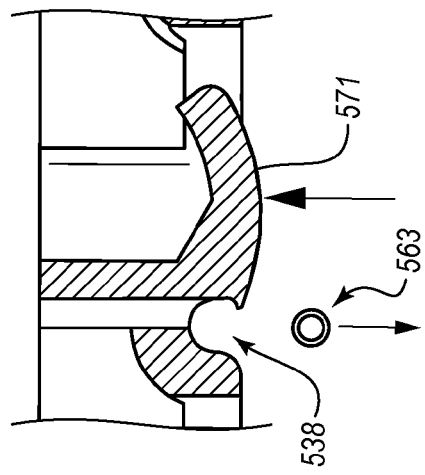
FIG. 11C is a cross-sectional overhead view of the device of FIG. 10C along the axes labeled 11B in a stage of removing a secondary introducer needle from a device for creating multiple access sites in a vessel.
Figure 11B:
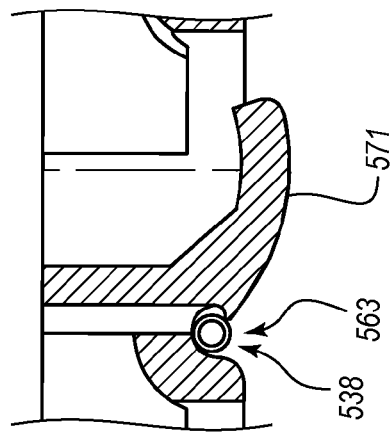
FIG. 11B is a cross-sectional overhead view of the device of FIG. 10C along the axes labeled 11B in a further stage of inserting a secondary introducer needle into a device for creating multiple access sites in a vessel.
Figure 11A:
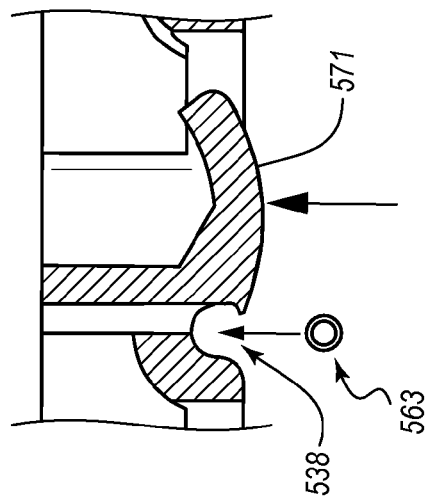
FIG. 11A is a cross-sectional overhead view of the device of FIG. 10C along the axes labeled 11B in an early stage of inserting a secondary introducer needle into a device for creating multiple access sites in a vessel.

FIGS. 11A, 11B and 11C depict in more detail the insertion of shaft 563 of secondary introducer needle 560 into the channel 538 comprising inner sidewall 539. FIG. 11A shows the transient opening of channel 538 upon depression at the arrow (corresponding to button 571), allowing for the disposition of shaft 563 into the channel via the lateral opening. FIG. 11B depicts the closure of channel 538 around the shaft 563, and contact between the sidewall and shaft 563. In the illustrated embodiment, a portion of the deflectable element may also contact shaft 563 to aid in retaining the shaft 563. FIG. 11C depicts the release of the shaft 563 of secondary introducer needle via the deflectable element, i.e. upon depression of the arrow (corresponding to button 571).

Figure 12B:
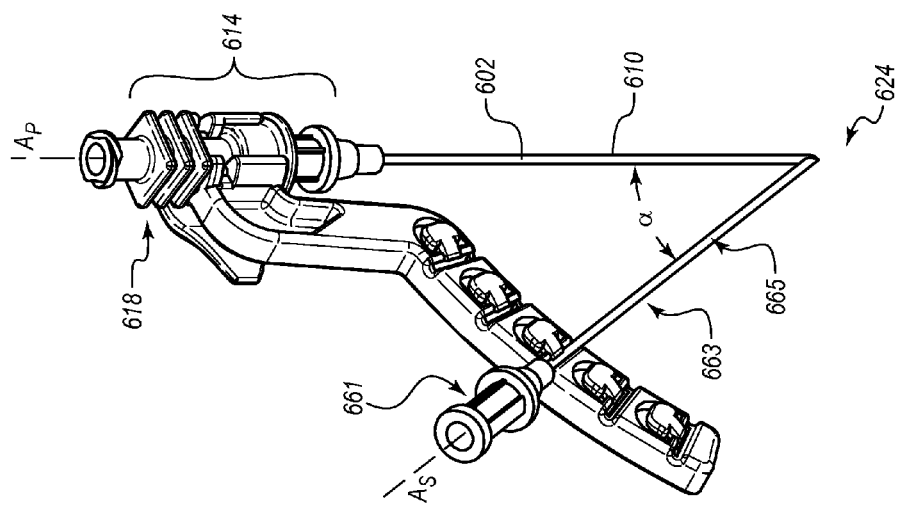
FIG. 12B is a perspective view of the device of FIG. 12A with a secondary introducer needle coupled to the device for creating multiple access sites in a vessel.
Figure 12A:
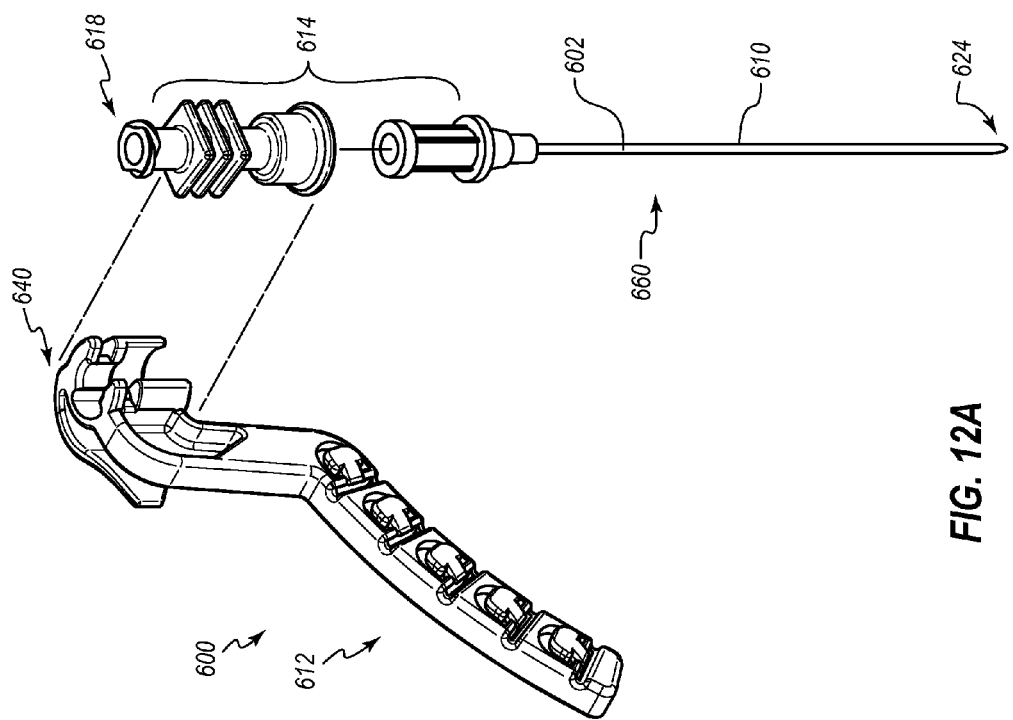
FIG. 12A is a perspective view of an additional embodiment of a primary introducer needle with a needle adapter coupled to a device for creating multiple access sites in a vessel.

FIG. 12A depicts another embodiment of a device 600 for creating multiple access sites in a vessel. The device 600 includes a hub 612 and an interface 640. A primary introducer needle 660 with a fluid channel or lumen 602, shaft 610, distal tip 624 has a connector 614 that is releasably coupled to hub 612. The connector 614, coupling the hub 612 with the primary introducer needle 660, however, varies somewhat from the connector 514 described above.

In the illustrated embodiment, connector 614 comprises, at its proximal end, a needle adapter 618, which is coupled to the primary introducer needle 660 with shaft 610, distal tip 624, and in fluid communication with lumen 602. The needle adapter 618 may be configured to accept any suitable primary introducer needle and hence, may be considered to be a universal adapter. In an embodiment, the needle adapter 618 may be coupled to hub 612 prior to insertion of the shaft 610 of the primary introducer needle 660.

In the illustrated embodiment, the connector 614 is configured to be releasably coupled with a connector of at the proximal end of the primary introducer needle 660. The connector of at the proximal end of the primary introducer needle 660 may be a standard male luer-type connector. The connector 614 may be configured to accept a male luer-type connector coupled to, or integrated within, the primary introducer needle. The connector 614 may, but does not necessarily, comprise a needle adapter 618 in order to couple the primary introducer needle to the hub 612 via interface 640.

FIG. 12B shows a primary and a secondary introducer needle present in an illustrative embodiment of a device 600 for creating multiple access sites in a vessel. In the illustrated embodiment, the shaft 610 of the primary introducer needle and the shaft 663 of the secondary introducer needle are angled relative to each other at angle α. Stated otherwise, the primary lumen 602 of the primary introducer needle comprising connector 614 with needle adapter 618, defines a longitudinal axis $A_P$ and the secondary lumen 665 of the secondary introducer needle defines a longitudinal axis $A_S$ that are angled relative to each other at an angle α. In certain embodiments, the longitudinal axes $A_P$, $A_S$ can be contained within the same plane, and/or may intersect.

Figure 13:
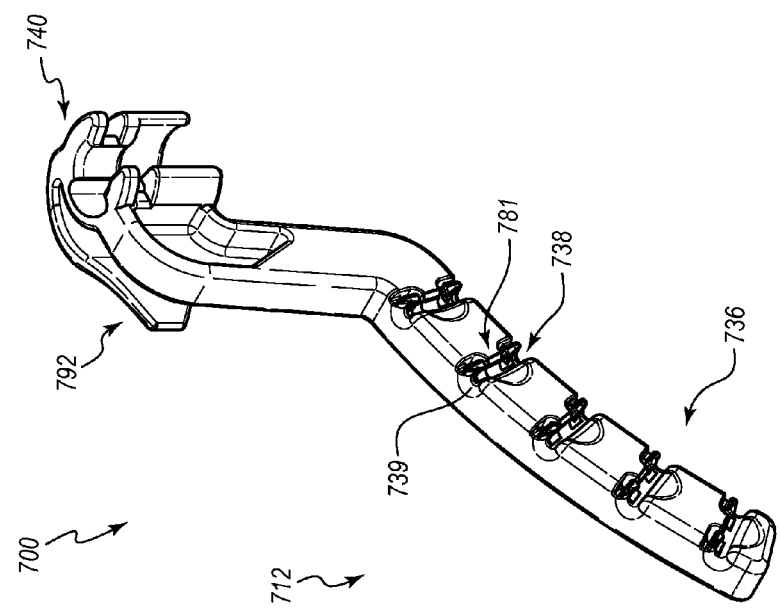
FIG. 13 is a perspective view of a further embodiment of a device for creating multiple access sites in a vessel.

FIG. 13 is a perspective view of an additional embodiment of a device 700 for creating multiple access sites in a vessel. The device 700 includes a hub 712, an interface 740 and a flange 792. The secondary region 736 of the device 700, however, varies somewhat from the secondary region 536 described above. The secondary region 736 can include a channel 738, which may be defined by a sidewall 739. The channel 738 may extend substantially perpendicular to the longitudinal axis of secondary region 736.

In the illustrated embodiment, the channel 738 has inner sidewall 739 which is not continuous but comprises voids or spaces in the sidewall to form at least one deformable bracket or rib 781. The deformable rib 781 comprises a deflectable element, which is configured to transiently expand the channel 738 to accept or release a secondary needle through a lateral opening. The deformable rib 781 is in communication with the channel 738. Depression of the hub at a position adjacent to deformable rib 781 by, for example, the practitioner's finger, moves the deflectable element such that the shaft of the secondary introducer needle can be disposed into the channel 738 laterally.

The deformable rib 781 may be configured to accept and provide sufficient force upon a secondary introducer needle such that the needle is free to move axially when the device 700 is used for any suitable purpose (e.g., aspiration, flushing, vascular access, etc.), to permit tactical feedback to a practitioner during the insertion or subsequent processes. As shown in FIG. 13, coupling of a secondary needle to the device 700 via channel 738 would occur laterally.

Figure 14A:
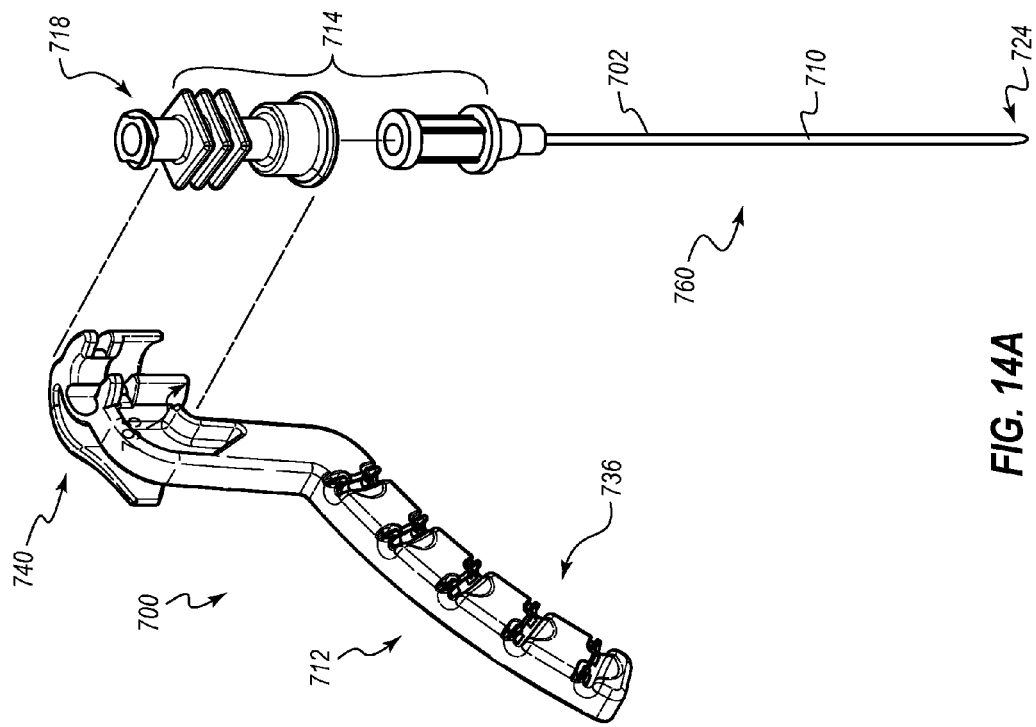
FIG. 14A is a perspective view of a primary introducer needle with a needle adapter being inserted into a further illustrative embodiment of a device for creating multiple access sites in a vessel.
Figure 14C:
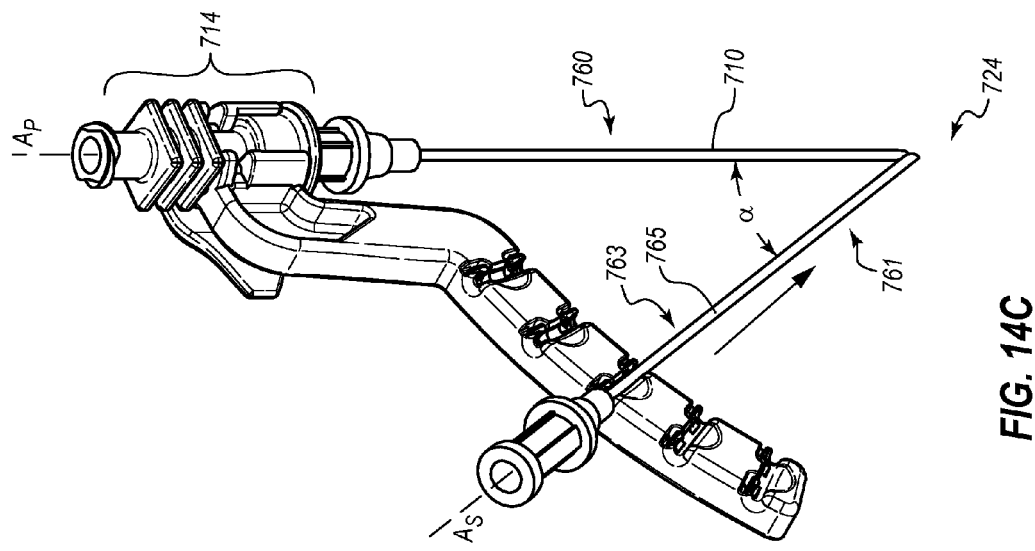
FIG. 14C is a perspective view of a primary introducer needle with a needle adapter and a secondary introducer needle present in a further illustrative embodiment of a device for creating multiple access sites in a vessel.
Figure 14B:
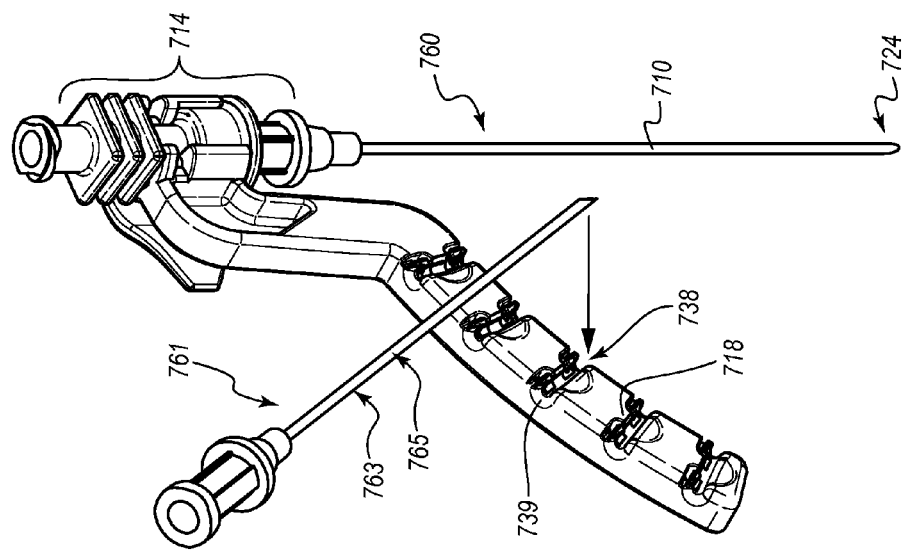
FIG. 14B is a perspective view of a secondary introducer needle being inserted into a further illustrative embodiment of a device for creating multiple access sites in a vessel, which already contains a primary introducer needle with a needle adapter.

FIGS. 14A, 14B and 14C depict the device 700 of FIG. 13 for creating multiple access sites in a vessel, showing the insertion of a primary introducer needle 760 and a secondary introducer needle 761. In the illustrated embodiment depicted in FIG. 14A, the device 700 includes a hub 712 and an interface 740. The primary introducer needle 760 includes a connector 714 comprising, at its proximal end, a needle adapter 718, which is coupled to the primary introducer needle 760 with shaft 710, distal tip 724, and in fluid communication with lumen 702. The needle adapter 718 may be configured to accept any suitable primary introducer needle. In an embodiment, the needle adapter may be coupled to hub 712 prior to insertion of the shaft 710 of the primary introducer needle 760.

FIG. 14B depicts the device 700 with the primary introducer needle 760 releasably coupled to the hub via connector 714 and interface 740, and shows the insertion of secondary introducer needle 761. In certain embodiments, the hub comprises a channel 738 comprising an inner sidewall 739. The channel 538 may be accessed by opening of a rib 781. The secondary introducer needle 761 can include a shaft 763 that defines a lumen 765. Secondary hub region 736 may be made of a material which is relatively rigid but flexible enough to allow for the temporary expansion of channel 738 with pressure applied by, for example, a practitioner's hand, to allow for the opening of the channel 738 to retain a shaft 763 of a secondary introducer needle 761 when the pressure is released. The inner sidewall 739 provides sufficient force upon the secondary needle 761 such that the needle is free to move axially when the device 700 is used for any suitable purpose (e.g., aspiration, flushing, vascular access, etc.), to permit tactical feedback to a practitioner during the insertion or subsequent processes.

In an embodiment, a depression or indentation in the secondary hub 736 may be present, adjacent to each channel 738. Similar to the button 571 in device 500, the depression or indentation is configured to accept pressure applied by, for example, a practitioner's finger, to open the channel 738 to insert and/or remove the shaft 763.

In other embodiments, the secondary needle 761 can be disposed into channel 738 and be retained within the channel. The secondary needle 761 may freely move along the secondary needle axis $A_S$ and the secondary needle shaft 763 may substantially maintain its orientation with the channel. After the secondary needle 761 is positioned in the vessel, a force may be applied to the secondary needle 761 relative to the hub 712 to dislodge and remove the needle 761 from the channel 738.

FIG. 14C depicts a primary and a secondary introducer needle present in an illustrative embodiment of a device 700 for creating multiple access sites in a vessel. The shaft 710 of primary introducer needle 760 and the shaft 763 of the secondary introducer needle 761 are angled relative to each other at an angle α. Stated otherwise, the primary lumen of primary introducer needle 760 can define a longitudinal axis $A_P$ and the secondary lumen of secondary introducer needle 761 can define a longitudinal axis $A_S$ that are angled relative to each other. In certain embodiments, the longitudinal axes $A_P$, $A_S$ can be contained within the same plane.

In some embodiments, the longitudinal axes $A_P$, $A_S$ can be configured to intersect, and may occur either with or without the shafts 710 and 763 coming in physical contact with each other. The device 700 may control the insertion depth of secondary needle shaft 763 relative to the position, depth and orientation of primary needle 760. In an embodiment, the device 700 may limit the insertion depth of a secondary needle 761 such that the distal tip of the secondary needle does not go beyond the depth of the distal tip 724 of the primary needle 710 or a guide wire inserted therethrough. In some embodiments, the primary needle shaft 710 may not be in physical contact with secondary needle shaft 763, but instead be disposed adjacent to or proximate to the shaft 763.

As previously mentioned, any suitable combination of the various features of the various embodiments is contemplated. For example, in some embodiments, the device 200 may have a permanently mounted shaft that extends distally from the primary region 232 of the hub 212, rather than a distal connector 216. Similarly, the devices 100, 300, 400 may have a distal connector in the place of a permanently mounted shaft. In certain embodiments, a secondary introducer needle 561 may be placed into the device 500 prior to placement of the primary introducer needle 560 via interface 540. In an embodiment, the device 700 comprising interface 740 may couple directly with a connector 714 of primary needle 760 that does not comprise a needle adapter 718.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub routines or only a portion of a method illustrated in the drawings, such as a small subset of step, may be a separate method. Stated otherwise, some additional methods may include only a portion of the steps shown in a more detailed method.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description. These additional embodiments are determined by replacing the dependency of a given dependent claim with the phrase "any of the preceding claims up to and including claim [x]," where the bracketed term "[x]" is replaced with the number of the most recently recited independent claim. For example, for the first claim set that begins with independent claim 1, claim 3 can depend from either of claims 1 and 2, with these separate dependencies yielding two distinct embodiments; claim 4 can depend from any one of claim 1, 2, or 3, with these separate dependencies yielding three distinct embodiments; claim 5 can depend from any one of claim 1, 2, 3, or 4, with these separate dependencies yielding four distinct embodiments; and so on.

Recitation in the claims of the term "first" with respect to a feature or element does not necessarily imply the existence of a second or additional such feature or element. Elements specifically recited in means-plus-function format, if any, are intended to be construed in accordance with 35 U.S.C. §112(f). Embodiments of the invention in which an exclusive property or privilege is claimed are defined as follows.

The invention claimed is:

1. A device for creating multiple access sites in an anatomical vessel, the device comprising:
   a first shaft that comprises a platform at a distal end thereof;
   a hub that either is coupled to or is configured to be coupled to the first shaft, wherein the hub is configured to be positioned at an exterior of a patient when the first shaft is coupled to the hub and is inserted into a vessel of the patient;
   a first channel coupled to the hub, wherein the first channel defines a first longitudinal axis that is configured to extend through a linear region of the first shaft when the first shaft is coupled to the hub; and
   a second channel coupled to the hub and spaced from the first channel, wherein the second channel defines a second longitudinal axis, and wherein the second channel is configured to permit a second shaft to extend therethrough,
   wherein a single plane contains the first and second longitudinal axes such that at least a portion of each of the first and second shafts can be positioned within a single vessel when the first shaft is coupled to the hub and the second shaft extends through the second channel, and wherein the platform of the first shaft is configured to stop a distal end of the second shaft at a position within the vessel when the second shaft is advanced through the second channel.

2. The device of claim 1, wherein the shaft comprises a hollow cylinder that comprises a notched region at a distal end thereof, and wherein the platform comprises an inner surface of the notched region.

3. The device of claim 1, wherein the platform is substantially semi-cylindrical.

4. The device of claim 1, wherein the first shaft comprises a bending region that permits the distal end of the shaft to bend relative to a proximal portion of the shaft and permits the platform to generally align with or be parallel to a longitudinal axis of the vessel.

5. The device of claim 4, wherein the first and second axes are parallel to each other.

6. The device of claim 1, wherein the first shaft comprises a bending region that permits the distal end of the shaft to bend relative to a proximal portion of the shaft.

7. The device of claim 1, wherein the first and second axes are at an angle relative to one another, wherein the first shaft is substantially linear, and wherein the second channel is configured to direct a distal end of the second shaft and stop proximate to the distal end of the first shaft when the distal end of the first shaft is within a vessel.

8. The device of claim 1, further comprising a third channel coupled to the hub that defines a third longitudinal axis that is within the single plane and is at an angle relative to the first longitudinal axis, wherein the second longitudinal axis is also at an angle relative to the first longitudinal axis, and wherein the angles between the first and third longitudinal axes and between the first and second longitudinal axes differ from one another.

9. The device of claim 1, further comprising a connector coupled to the hub, wherein the connector is configured to be coupled with a connector of an introducer needle.

10. A device for creating multiple access sites in an anatomical vessel, the device comprising:
a first shaft that comprises a platform configured to be inserted into the anatomical vessel;
a hub that either is coupled to or is configured to be coupled to the first shaft, and the hub either is coupled to or is configured to be coupled to a second shaft;
wherein the hub is configured to be positioned at an exterior of a patient when the first shaft is coupled to the hub and is inserted into a vessel of the patient;
wherein the hub maintains the first shaft and the second shaft in a position such that a the first shaft defines a first longitudinal axis and the second shaft defines a second longitudinal axis;
wherein a single plane contains the first and second longitudinal axes such that at least a portion of each of the first and second shafts can be positioned within the anatomical vessel; and
wherein the platform is configured to contact a distal end of the second shaft to prevent the tip from passing through a back wall of the anatomical vessel.

11. The device of claim 10, wherein the hub comprises a lateral opening that is configured to permit the second shaft to be disposed in the hub via the lateral opening.

12. The device of claim 10, wherein the hub comprises an interface for receiving a connector for the first shaft.

13. The device of claim 12, wherein the connector for the first shaft is releasably coupleable from the interface, and wherein the connector is configured to be coupled to the first shaft.

14. The device of claim 13, wherein the connector defines a lumen that is in fluid communication with the first shaft.

15. The device of claim 13, wherein the connector is configured to be coupled with a connector of an introducer needle.

16. The device of claim 10, wherein the hub comprises an interface for receiving a needle adapter comprising the first shaft.

17. A device for creating multiple access sites in an anatomical vessel, the device comprising:
a first shaft that comprises a platform configured to be inserted into the anatomical vessel;
a hub that either is coupled to or is configured to be coupled to the first shaft, wherein the hub is configured to be positioned at an exterior of a patient when the first shaft is coupled to the hub and is inserted into a vessel of the patient;
a first channel coupled to the hub, wherein the first channel defines a longitudinal axis that is configured to extend through a linear region of the first shaft when the first shaft is coupled to the hub; and
a second channel coupled to the hub and spaced from the first channel, wherein the second channel defines a second longitudinal axis, and wherein the second channel is configured to permit a second shaft to extend therethrough,
wherein the first and second longitudinal axes are configured to intersect, and wherein the platform is configured to prevent a distal tip of the second shaft from passing through a back wall of the anatomical vessel.

18. The device of claim 17, wherein the first and second longitudinal axes are configured to intersect at a position that is at an interior of a vessel when the first shaft is coupled to the hub and a portion of the first shaft is positioned within the vessel.

19. A method of creating multiple access sites in a vessel, the method comprising:
inserting a portion of a first shaft through the skin of a patient and into an interior of the vessel at a first access site, wherein the first shaft is coupled to a hub at a position exterior to the patient; and
inserting a second shaft into a channel defined by the hub, then through the skin of the patient, and then into the interior of the vessel and into contact with the portion of the first shaft that is at the interior of the vessel at a second access site while the first shaft remains coupled with the hub.

20. The method of claim 19, wherein the first shaft comprises a platform at a distal end thereof, and wherein said inserting the second shaft into the interior of the vessel comprises contacting the platform with a distal end of the second shaft within the vessel.

21. The method of claim 19, further comprising coupling the first shaft to the hub, wherein the first shaft comprises an introducer needle, wherein the hub maintains the first shaft and the second shaft in a position such that the first shaft defines a first longitudinal axis and the second shaft defines a second longitudinal axis; and wherein a single plane contains the first and second longitudinal axes such that at least a portion of each of the first and second shafts can be positioned within the vessel.

22. The method of claim 19, wherein inserting the second shaft into the channel defined by the hub comprises advancing the second shaft at an angle relative to the first shaft.

23. The method of claim 19, further comprising inserting a third shaft into an additional channel defined by the hub, then through the skin of the patient, and then into the interior of the vessel at a third access site while the first shaft remains coupled with the hub.

24. The method of claim 19, wherein inserting the portion of the first shaft through the skin of a patient and into an interior of the vessel at a first access site comprises imaging at least a portion of the patient to achieve a desired placement of the first shaft within the vessel, and wherein inserting a distal end of a second shaft into the interior of the vessel at a second access site is achieved without any further imaging of the patient.

25. The method of claim 19, wherein the first shaft comprises a bending region, the method further comprising bending the first shaft at the bending region to bring a distal end of the first shaft into general alignment or parallelism with a longitudinal axis of the vessel.

* * * * *